(12) United States Patent
Pawliszyn

(10) Patent No.: US 8,598,325 B2
(45) Date of Patent: Dec. 3, 2013

(54) SOLID-PHASE MICROEXTRACTION COATINGS AND METHODS FOR THEIR PREPARATION

(76) Inventor: Janusz B. Pawliszyn, Waterloo (CA)

( * ) Notice: Subject to any disclaimer, the term of this patent is extended or adjusted under 35 U.S.C. 154(b) by 0 days.

(21) Appl. No.: 13/412,122

(22) Filed: Mar. 5, 2012

(65) Prior Publication Data

US 2012/0164286 A1 Jun. 28, 2012

Related U.S. Application Data

(63) Continuation-in-part of application No. 12/174,494, filed on Jul. 16, 2008, which is a continuation-in-part of application No. 11/706,167, filed on Feb. 15, 2007, now Pat. No. 8,008,064, which is a continuation of application No. 11/208,933, filed on Aug. 23, 2005, now Pat. No. 7,232,689, which is a continuation-in-part of application No. 10/506,827, filed as application No. PCT/CA03/00311 on Mar. 6, 2003, now Pat. No. 7,384,794.

(60) Provisional application No. 60/364,214, filed on Mar. 11, 2002, provisional application No. 60/393,309, filed on Jul. 3, 2002, provisional application No. 60/421,001, filed on Oct. 25, 2002, provisional application No. 60/421,510, filed on Oct. 28, 2002, provisional application No. 60/427,833, filed on Nov. 21, 2002.

(51) Int. Cl.
*C07K 1/14* (2006.01)
*G01N 33/538* (2006.01)

(52) U.S. Cl.
USPC .......................... 530/415; 530/412; 436/541

(58) Field of Classification Search
None
See application file for complete search history.

(56) References Cited

U.S. PATENT DOCUMENTS

| | | | |
|---|---|---|---|
| 4,476,231 A | 10/1984 | Deindoerfer et al. |
| 4,616,652 A | 10/1986 | Simpson |
| 5,120,510 A | 6/1992 | Gourley et al. |
| 5,424,187 A | 6/1995 | Shor et al. |
| 5,460,813 A | 10/1995 | Leung et al. |
| 5,464,395 A | 11/1995 | Faxon et al. |
| 5,479,923 A | 1/1996 | Rantala |
| 5,640,470 A | 6/1997 | Iyer et al. |
| 5,691,206 A | 11/1997 | Pawliszyn |
| 5,693,228 A | 12/1997 | Koehler et al. |
| 6,287,521 B1 | 9/2001 | Quay et al. |
| 6,360,588 B1 | 3/2002 | Ross et al. |
| 6,558,958 B1 | 5/2003 | Pilevar et al. |
| 6,689,603 B2 | 2/2004 | Pompidou et al. |
| 6,730,096 B2 | 5/2004 | Basta |
| 6,743,180 B1 | 6/2004 | Van Bockel |
| 6,808,937 B2 | 10/2004 | Ligler et al. |
| 6,871,556 B2 | 3/2005 | Andresen et al. |
| 7,232,689 B2 | 6/2007 | Pawliszyn |
| 7,259,019 B2 | 8/2007 | Pawliszyn et al. |
| 7,384,794 B2 | 6/2008 | Pawliszyn |
| 7,468,281 B2 | 12/2008 | Kallury et al. |
| 7,605,003 B2 | 10/2009 | Chan et al. |
| 2002/0034827 A1 | 3/2002 | Singh et al. |
| 2003/0135195 A1 | 7/2003 | Jimenez et al. |
| 2003/0180954 A1 | 9/2003 | Riviere et al. |
| 2003/0183758 A1 | 10/2003 | Colburn et al. |
| 2004/0005582 A1 | 1/2004 | Shipwash |
| 2004/0171169 A1 | 9/2004 | Kallury et al. |
| 2005/0032237 A1 | 2/2005 | Sandra et al. |
| 2005/0142033 A1 | 6/2005 | Glezer et al. |

FOREIGN PATENT DOCUMENTS

| | | |
|---|---|---|
| DE | 19905239 | 8/2000 |
| JP | 11-64277 | 3/1999 |
| WO | 91/15745 | 10/1991 |
| WO | 00/68665 | 11/2000 |

OTHER PUBLICATIONS

Shirey et al. Optimization of extraction conditions and fiber selection for semivolatile analytes using solid-phase microextraction. Journal of CHromatographic Science 2000, vol. 38, pp. 279-288.*
Lambropoulou et al. Validation of an SPME method, using PDMS, PA, PDMS-DVB, and CW-DVB SPME fiber coatings, for analysis of organophosphorous insecticides in natural water. Anal Bioanal Chem 2002, vol. 374, pp. 932-941.*
Mullett et al. Direct determination of benzodiazepines in biological fluids by restricted-access solid-phase microextraction. Anal. Chem. 2002, vol. 74, pp. 1081-1087.*
Mindrup et al. Improved performance of SPME fibers and applications. SUPELCO 2001, Sigma-Aldrich Co. 2001,. pp. 1-25.*
Yang et al., "Surface Modification and Blood Compatibility of Polyacrylonitrile Membrane with Immobilized Chitosan-Heparin Conjugate", Journal of Polymer Research, Nov. 3, 2002, vol. 9, Issue 3, pp. 201-206, http://www.springerlink.com/content/m2878p248r41nk81/.
Zhang et al., "Solid-Phase Microextraction", Analytical Chemistry, Sep. 1, 1994, vol. 66, No. 17, pp. 844-853.

(Continued)

*Primary Examiner* — Shafiqul Haq
(74) *Attorney, Agent, or Firm* — David A. Nauman; Borden Ladner Gervais LLP

(57) ABSTRACT

There is described a coated solid phase microextraction (SPME) fiber for use in direct immersion SPME of a food matrix that includes carbohydrates. The coated SPME fiber includes a SPME fiber for absorbing a small molecule from the food matrix; and a protective coating which has a surface that is substantially uniform and substantially smooth, the protective coating reducing adsorption of the carbohydrates onto the SPME fiber and allowing the SPME fiber to extract the small molecule from the food matrix. A process for producing the coated SPME fiber and a method of performing solid phase microextraction are also described.

15 Claims, 12 Drawing Sheets

(56) References Cited

OTHER PUBLICATIONS

U.S. Appl. No. 12/939,360, Office Action dated Apr. 4, 2011.
Gonzalez-Rodriguez et al., "Multiresidue determination of 11 new fungicides in grapes and wines by liquid-liquid extraction/clean-up and programmable temperature vaporization injection with analyte protectants/gas chromatography/ion trap mass spectrometry", Journal of Chromatography A., Aug. 7, 2009, vol. 1216, Issue 32, pp. 6033-6042.
Banerjee et al., "Validation and uncertainty analysis of a multi-residue method for pesticides in grapes using ethyl acetate extraction and liquid chromatography-tandem mass spectrometry", Journal of Chromatography A, Nov. 30, 2007, vol. 1173,1-2, pp. 98-109.
Guillet et al., "Microwave/SPME method to quantify pesticides residues in tomato fruits", Journal of Environmental Science and Health Part B, Jun. 2009, vol. 44, Issue 5, pp. 415-422.
Oliva et al., "Multiresidue method for the rapid determination of organophosphorous insecticides in grapes, must and wine", Journal of Chromatography A, Jun. 16, 2000, vol. 882, Issue 1-2, pp. 213-220.
Oliva et al., "Determination of chlorpyrifos, penconazole, fenarimol, vinclozolin and metalaxyl in grapes, must and wine by on-line microextraction and gas chromatogaphy", Journal of Chromatography A, Feb. 12, 1999, vol. 833, Issue 1, pp. 43-51.
Charlton et al., "Determination of imidazole and triazole fungicide residues in honeybees using gas chromatography-mass spectrometry", Journal of Chromatography A, Feb. 2, 2007, vol. 1141, Issue 1, pp. 117-122.
Zeng et al., "Development of polytimethylphenylsiloxane-coated fiber for solid-phase microextraction and its analytical application of qualitative and semi-quantitative of organochlorine and pyrethroid pesticides in vegetables", Analytica Chimica Acta, Jun. 30, 2008, vol. 619, Issue 1, pp. 59-66.
Anastassiades et al., "Fast and easy multiresidue method employing acetonitrile extraction/partitioning and "dispersive solid-phase extraction" for the determination of pesticide residues in produce", Journal of AOAC International, Mar.-Apr., 2003, vol. 86, Issue 2, pp. 412-431.
Steiniger et al., "Determination of Multiresidue Pesticides in Green Tea by Using a Modified QuEChERS Extraction and Ion-Trap Gas Chromatography/Mass Spectrometry", Journal of AOAC International, Jul.-Aug., 2010, vol. 93, Issue 4, pp. 1169-1179.
Cunha et al., "Fast low-pressure gas chromatography-mass spectrometry method for the determination of multiple pesticides in grapes, musts and wines", Journal of Chromatography A, Jan. 2, 2009, vol. 1216, Issue 1, pp. 119-126.
Wong et al., "Development and Interlaboratory Validation of a QuEChERS-Based Liquid Chromatography-Tandem Mass Spectrometry Method for Multiresidue Pesticide Analysis", Journal of Agricultural and Food Chemistry, 2010, (available on-line Mar. 2, 2010 ), vol. 58, Issue 10, pp. 5897-5903.
Paya et al., "Analysis of pesticide residues using the Quick Easy Cheap Effective Rugged and Safe (QuEChERS) pesticide multiresidue method in combination with gas and liquid chromatography and tandem mass spectrometric detection", Analytical and Bioanalytical Chemistry, Nov. 2007, vol. 389, Issue 6, pp. 1697-1714.
Pawliszyn, "SPME Method Development. Solid Phase Microextraction: Theory and Practice", New York : Wiley-VCH, 1997, pp. 97-139.
Risticevic et al., "Protocol for solid phase microextraction method development", Nature Protocols, 2010, (available on-line Jan. 7, 2010), vol. 5, pp. 122-139.
Schurek et al., "Application of head-space solid-phase microextraction coupled to comprehensive two-dimensional gas chromatography-time-of-flight mass spectrometry for the determination of multiple pesticide residues in tea samples", Analytica Chimica Acta, Mar. 24, 2008, vol. 611, Issue 2, pp. 163-172.
Lambropoulou et al., "Headspace solid-phase microextraction in combination with gas chromatography-mass spectrometry for the rapid screening of organophosphorus insecticide residues in strawberries and cherries", Journal of Chromatography A, Apr. 18, 2003, vol. 993, Issues 1-2, pp. 197-203.
Natangelo et al., "Evaluation of solid phase microextraction-gas chromatography in the analysis of some pesticides with different mass spectrometric techniques: Application to environmental waters and food samples", Analytical Letters, 2002, (available on-line Feb. 2, 2007), vol. 35, Issue 2, pp. 327-338.
Chen et al., "The application of solid phase microextraction in the analysis of organophosphorous pesticides in a food plant", Environmental Science & Technology, 1998, (available on-line Oct. 2, 1998), vol. 32, Issue 23, pp. 3816-3820.
Fytianos et al., "Solid phase microextraction applied to the analysis of organophosphorous insecticides in fruits", Chemosphere, Dec. 2006, vol. 65, Issue 11, pp. 2090-2095.
Filho et al., "Development, validation and application of a methodology based on solid-phase micro extraction followed by gas chromatography coupled to mass spectrometry (SPME/GC-MS) for the determination of pesticides residues in mangoes", Talanta, Apr. 15, 2010, vol. 81, pp. 346-354.
Volante et al., "Application of solid phase microextraction (SPME) to the analysis of pesticides residues in vegetables", Pest Management Science, Jul. 2000, vol. 56, Issue 7, pp. 618-636.
Capobiango et al., "A solid-phase microextraction method for the chromatographic determination of organophosphorous pesticides in fish, water, potatoes, guava and coffee", Journal of Brazilian Chemical Society, Sep.-Oct. 2005, vol. 16, Issue 5, pp. 907-914.
Zambonin et al., "Solid-phase microextraction—gas chromatography mass spectrometry: A fast and simple screening method for the assessment of organophosphorous pesticides residues in wine and fruit juices", Food Chemistry, Jun. 2004, vol. 86, Issue 2, pp. 269-274.
Zambonin et al., "Solid-phase microextraction and gas chromatography-mass spectrometry for the rapid screening of triazole residues in wine and strawberries", Journal of Chromatography A, Aug. 23, 2002, vol. 967, Issue 2, pp. 255-260.
Aguinaga et al., "Solid phase microextraction coupled to gas chromatography-mass spectrometry for the analysis of famoxadone in wines, fruits and vegetables", Spectroscopy Letters, 2009, (available on-line Dec. 1, 2009), vol. 42, Issue 6-7, pp. 320-326.
Hu et al., "Solid phase microextraction of pesticide residues from strawberries", Food Additives and Contaminants, 1999, (available on-line Nov. 10, 2010), vol. 16, Issue 3, pp. 111-117.
Vinas et al., "Method development and validation for strobilurin fungicides in baby foods by solid-phase microextraction gas chromatography-mass spectrometry", Journal of Chromatography A, Jan. 2, 2009, vol. 1216, Issue 1, pp. 140-146.
Ridgway et al., "Sample preparation techniques for the determination of trace residues and contaminants in food", Journal of Chromatography A, Jun. 15, 2007, vol. 1153, Issue 1-2, pp. 36-53.
Augusto et al., "New sorbents for extraction and microextraction techniques", Journal of Chromatography A, Apr. 16, 2010, vol. 1217, Issue 16, pp. 2533-2542.
Cai et al., "Vinyl crown ether as a novel radical crosslinked sol-gel SPME fiber for determination of organousphosphorous pesticides in food samples", Analytica Chimica Acta, Feb. 10, 2006, vol. 559, Issue 1, pp. 89-96.
Djozan et al., "Preparation and binding study of solid-phase microextraction fiber on the basis of ametryn-imprinted polymer— Application to the selective extraction of persistent triazine herbicides in tap water, rice, maize and onion", Journal of Chromatography A, Mar. 20, 2009, vol. 1216, Issue 12, pp. 2211-2219.
Turiel et al., "Molecularly imprinted polymeric fibers for solid-phase microextraction", Analytical Chemistry, Apr. 15, 2007, vol. 79, Issue 8, pp. 3099-3104.
Dietz et al., "Recent developments in solid-phase microextarction coatings and related techniques", Journal of Chromatography A, Jan. 27, 2006, vol. 1103, Issue 2, pp. 183-192.
Beltran et al., "Solid-phase microextraction in pesticide residue analysis", Journal of Chromatography A, Jul. 14, 2000, vol. 885, Issue 1-2, pp. 389-404.

(56) References Cited

OTHER PUBLICATIONS

Jahnke et al., "Do complex matrices modify the sorptive properties of polydimethylsiloxane (PDMS) for non-polar organic chemicals?", Journal of Chromatography A, Jul. 16, 2010, vol. 1217, Issue 29, pp. 4765-4770.

Vuckovic et al., "In vitro evaluation of new biocompatible coatings for solid-phase microextraction: Implications for drug analysis and in vivo sampling applicatons", Analytica Chimica Acta, Apr. 13, 2009, vol. 638, Issue 2, pp. 175-185.

De Jager et al., "Analysis of tetramethylene disulfotetramine in foods using solid-phase microextraction-gas chromatography-mass spectrometry", Journal of Chromatography A, May 23, 2008, vol. 1192, Issue 1, pp. 36-40.

Simplicio et al., "Validation of a solid-phase microextraction method for the determination of organophosphorous pesticides in fruits and fruit juice", Journal of Chromatography A, Feb. 12, 1999, vol. 833, Issue 1, pp. 35-42.

Kloskowski et al., "Membrane solid-phase microextraction—A new concept of sorbent preparation", Analytical Chemistry, 2009, (available on-line Aug. 4, 2009), vol. 81, Issue 17, pp. 7363-7367.

Japanese Patent Application No. 574050/2003, Office Action dated Feb. 10, 2009.

Frerot et al., "Solid-Phase Microextraction (SPME): A New Tool in Pheromone Identification in Lepidoptera", J. High Resolut. Chromatogr, Jun. 1997, vol. 20, Issue 6, pp. 340-342.

Heinze, "Ultramicroelectrodes in Electrochemistry", Angew. Chem. Int. Ed. Engl., Sep. 1993, vol. 32, Issue 9, pp. 1268-1288.

Jackson et al., "Mass spectrometry for genotyping: an emerging tool for molecular medicine", Molecular Medicine Today, Jul. 1, 2000, vol. 6, Issue 7, pp. 271-276.

Lavaud et al., "Optimal anticoagulation strategy in haemodialysis with heparin-coated polyacrylonitrile membrane", Nephrology Dialysis Transplantation, Oct. 2003, vol. 18, Issue 10, pp. 2097-2104, available http://ndt.oxfordjournals.org/cgi/content/abstract/18/10/2097.

Lord et al., "Development and Evaluation of a Solid-Phase Microextraction Probe for in Vivo Pharmacokinetic Studies", Anal. Chem., Oct. 1, 2003, vol. 75, Issue 19, pp. 5103-5115.

Moneti et al., "Solid-Phase Microextraction of Insect Epicuticular Hydrocarbons for Gas Chromatographic/Mass Spectrometric Analysis", Rapid Communications in Mass Spectometry, May 1997, vol. 11, Issue 8, pp. 857-862.

Namera et al., "Analysis of anatoxin-a in aqueous samples of solid-phase microextraction coupled to high-performance liquid chromatography with fluorescence detection and on-fiber derivatization", Journal of Chromatography A, Jul. 19, 2002, vol. 963, Issue 1, pp. 295-302.

Nie et al., "Preparation and Characterization of polyacrylonitrile-based membranes: Effects of internal coagulant on poly (acrylonitrileco-malefic acid) ultrafiltration hollow fiber membranes", Desalination, Jan. 5, 2004, vol. 160, Issue 1, pp. 43-50.

Smith et al., "Solid-Phase Microextraction as a Tool for Studying Volatile Compounds in Frog Skin", Chemistry and Ecology, 2000 (available on-line Sep. 24, 2006), vol. 17, Issue 3, pp. 215-225.

Whang et al., "Solid phase microextraction coupled to capillary electrophoresis", Anal. Commun., 1998, vol. 35, Issue 11, pp. 353-356.

\* cited by examiner

SOLID-PHASE MICROEXTRACTION COATINGS AND METHODS FOR THEIR PREPARATION

CROSS REFERENCE TO RELATED APPLICATIONS

This application is a continuation-in-part of U.S. patent application Ser. No. 12/174,494 filed Jul. 16, 2008. U.S. patent application Ser. No. 12/174,494 is a continuation-in-part of U.S. patent application Ser. No. 11/706,167, filed Feb. 15, 2007 (now U.S. Pat. No. 8,008,064), which is a continuation of U.S. patent application Ser. No. 11/208,933 filed Aug. 23, 2005 (now U.S. Pat. No. 7,232,689), which is a continuation-in-part of U.S. patent application Ser. No. 10/506,827 filed Sep. 7, 2004 (now U.S. Pat. No. 7,384,794) which is derived from International Patent Application PCT/CA2003/000311, which claims benefit of U.S. Patent Application 60/364,214 filed Mar. 11, 2002; U.S. Patent Application 60/393,309 filed Jul. 3, 2002; U.S. Patent Application 60/421,001 filed Oct. 25, 2002; U.S. Patent Application 60/421,510 filed Oct. 28, 2002; and U.S. Patent Application 60/427,833 filed Nov. 21, 2002. The entirety of each of the above-mentioned documents being incorporated herein by reference.

FIELD

The present disclosure relates to coatings for sampling devices used for microextraction of components of interest in a matrix that includes carbohydrates for further quantification or identification.

BACKGROUND

Microextraction is a significant departure from conventional 'sampling' techniques. In conventional sampling techniques, a portion of the system under study is removed from its natural environment and the compounds of interest extracted and analyzed in a laboratory environment. In microextraction, compounds of interest are not exhaustively removed from the investigated system, and conditions can be devised where only a small proportion of the total amount of compound, and none of the matrix, are removed. This avoids disturbing the normal balance of chemical components. Because extracted chemicals can be separated chromatographically and quantified by highly sensitive analytical instruments, high accuracy, sensitivity and selectivity are achieved.

With current commercially available solid phase microextraction (SPME) devices, a stationary extraction phase is coated onto a fused silica fibre. The coated portion of the fibre is typically about 1 cm long and coatings have various thicknesses. The fibre can be mounted into a stainless steel support tube and housed in a syringe-like device for ease of use. Extractions are performed by exposing the extraction phase to a sample for a pre-determined time to allow sample components to come into equilibrium with the extraction phase. After extraction, the fibre is removed to an analytical instrument (typically a gas or liquid chromatograph) where extracted components are desorbed and analysed. The amount of a component extracted is proportional to its concentration in the sample (J. Pawliszyn "Method and Device for Solid Phase Microextraction and Desorption", U.S. Pat. No. 5,691,206.).

To date, commercial SPME devices have been used in some applications of direct analysis of living systems. For example they have been applied for the analysis of airborne pheromones and semiochemicals used in chemical communications by insects (Moneti, G.; Dani, F. R.; Pieraccini, G. T. S. Rapid Commun. Mass Spectrom. 1997, 11, 857-862.), (Frerot, B.; Malosse, C.; Cain, A. H. J. High Resolut. Chromatogr. 1997, 20, 340-342.) and frogs (Smith, B. P.; Zini, C. A.; Pawliszyn, J.; Tyler, M. J.; Hayasaka, Y.; Williams, B.; Caramao, E. B. Chemistry and Ecology 2000, 17, 215-225.) respectively. In these cases, the living animals were non-invasively monitored over time by assessing the chemical concentrations in the air around the animal, providing a convenient means to study complicated dynamic processes without interference.

The current commercial devices do, however, have some limitations for in vivo and in vitro analysis of a biological matrix, such as blood or tissue. Firstly, the most difficult and undesirable problem is the adsorption of proteins and other macromolecules on the surface of SPME fibres. Devices can be made biocompatible by coating them with a biocompatible material. Custom-made coatings based on polypyrrole (PPY) (Lord, H. L.; Grant, R. P.; Walles, M.; Incledon, B.; Fahie, B.; Pawliszyn, J. B., Anal. Chem. 2003, 75(19), 5103-5115) and poly(ethylene glycol) (PEG) (Musteata, F. M.; Musteata, M. L.; Pawliszyn, J., Clin Chem 2006, 52(4), 708-715) have been used for in vivo drug analysis.

Other materials which have been used to reduce the adsorption of proteins and other macromolecules found in a biological matrix include: restricted access materials (RAM), ionic liquids (IL), polydimethylsiloxane (PDMS), polypyrrole, and poly(ethylene glycol). Biocompatible membranes have also been prepared from polyacrylonitrile (Nie, F.-Q.; Xu, Z.-K.; Ming, Y.-Q.; Kou, R.-Q.; Liu, Z.-M.; Wang, S.-Y. Desalination 2004, 160, 43-50. Lavaud, S.; Canivet, E.; Wuillai, A.; Maheut, H.; Randoux, C.; Bonnet, J.-M.; Renaux, J.-L.; Chanard, J. Nephrology, Dialysis, Transplantation 2003, 18, 2097-2104. Yang, M. C.; Lin, W. C. Journal of Polymer Research 2002, 9, 201-206), polyurethane, chitosan, and cellulose.

As noted above, in analysis of chemicals in a biological matrix, such as blood or tissue, the most difficult and undesirable problem is the adsorption of proteins and other macromolecules on the surface of SPME fibres. In contrast, in the analysis of chemicals in vegetable, fruit or food processing, such as fruit juices, the most difficult and undesirable problem is the adsorption of carbohydrates on the surface of SPME fibres. Adsorbed carbohydrates may be transformed into carbon deposits when heated in analytical instruments, such when used for gas chromatography.

Conventional methods of sample preparation used in analysis of pesticides residues in vegetable, fruit and food processing may include liquid-liquid extractions, microwave assisted extraction, supercritical fluid extraction, on-line microextraction, or solid-phase extraction. These methods can be time-consuming, tedious and hazardous to operators' health, for example due to the organic solvents involved.

Another method used in analysis of pesticides residues in vegetable, fruit and food processing includes an extraction procedure based on liquid-liquid partitioning with acetonitrile followed by a cleanup step with dispersive-SPE (solid phase extraction), was described by Anastassiades et al. (*Journal of AOAC International.* 2003, Vol. 86, 2, pp. 412-431). This method has been applied in multi-residue analysis of pesticides in fruits and vegetables. However, the method is a multistep method and cannot be automated. The combination of sample preparation and instrument introduction steps is not accomplished by this method. Furthermore, this sample preparation technique uses multistep, labor-intensive procedure and requires the use of organic solvents.

It is desirable to develop an automated methodology to analyze pesticides in food matrices, for example using a high sample throughput with the entire analysis being completely automated. Solid-phase microextraction (SPME), which integrates sampling, extraction, concentration and sample introduction into a single step may be used to facilitate rapid sample preparation and integrate sampling, extraction, concentration and sample introduction to an analytical instrument into one solvent-free step. However, the facilitation of high-quality analytical methods in combination with SPME requires optimization of the parameters that affect the extraction efficiency; namely, extraction phase chemistry, extraction mode, agitation method, sample modification (pH, ionic strength, organic solvent content), sample temperature, extraction time and desorption conditions (*Nature Protocols.* 2010, Vol. 5, 1, pp. 122-139).

SPME has been used in the extraction of pesticides residues in vegetal foodstuff. However, food applications usually use headspace-SPME (HS-SPME), in which the extraction phase is placed in the headspace above the sample, rather than immersed into the sample. One limitation of this approach is that the rates of extraction are low for poorly volatile or polar analytes.

Another SPME method which has been used is direct immersion SPME (DI-SPME). Due to the complex nature of food matrices, DI-SPME can be difficult and is typically a poor choice for food analysis, especially when using solid sorbents (L. S De Jager, G. A. Perfetti, G. W. Diachenko. Analysis of tetramethylene disulfotetramine in foods using solid-phase microextraction-gas chromatography-mass spectrometry. *Journal of Chromatography A.* 2008, Vol. 1192, pp. 36-40). DI-SPME can be difficult because pretreatment of the sample may be necessary to protect the coating and avoid the fouling of the extraction phase by irreversible adsorption of macromolecules from the complex matrix at the interface. Such fouling could lead to a substantial decrease in the fibre lifetime, making it unusable for more than a few samples, and could also change the coating extraction properties (*Journal of Chromatography A.* 2007, Vol. 1153, pp. 36-53). The additional pretreatment or clean-up prior to SPME extraction may include, for example, centrifugation, dilution or pre-extraction in organic solvent.

It is desirable to provide a SPME fibre to be used in SPME, for example in DI-SPME or HS-SPME, where the SPME fibre is able to extract small molecules from a vegetable, fruit or food matrix, and where the SPME fibre has a protective coating which reduces adsorption of carbohydrates on the surface of the coated SPME fibres in comparison to a non-protectively coated SPME fibre. Additionally, it is desirable to provide a coating which is stable to chromatographic techniques used to analyze the extracted small molecules. Additionally, it is desirable to provide a process for coating an SPME fibre with said such a protective coating.

SUMMARY

It is an object of the present disclosure to obviate or mitigate at least one disadvantage of previous extraction coatings.

In a first aspect, the present disclosure provides a coated solid phase microextraction (SPME) fibre for use in direct immersion SPME of a food matrix that includes carbohydrates. The coated SPME fibre includes: a SPME fibre for absorbing a small molecule from the food matrix; and a protective coating which has a surface that is substantially uniform and substantially smooth surface, the protective coating reducing adsorption of the carbohydrates onto the SPME fibre and allowing the SPME fibre to extract the small molecule from the food matrix. The surface may also be substantially non-porous.

The protective coating may include polydimethylsiloxane (PDMS) or polyfluorocarbons. The SPME fibre may be a commercially available SPME fibre. Alternatively, the SPME fibre may include a bonding polymer adhering together SPME particles which have pores for absorbing the small molecule from the food matrix.

The protective coating may have, on average: fewer than 2 imperfections greater than 10 nm in length per 1000 $nm^2$ of protective coating, as seen on a 900× magnification of an Electron Scanning Microscope, fewer than 1 imperfections greater than 10 nm in length per 1000 $nm^2$ of protective coating, as seen on a 900× magnification of an Electron Scanning Microscope, or fewer than 0.1 imperfections greater than 10 nm in length per 1000 $nm^2$ of protective coating, as seen on a 900× magnification of an Electron Scanning Microscope. In some examples, the protective coating may have no observable defects when viewed at 900× magnification using an Electron Scanning Microscope.

The food matrix may be selected from the group consisting of fruit pulp, fruit juice, vegetable pulp, vegetable juice, and any combination thereof.

The small molecule may be a hydrophobic or hydrophilic molecule having a molecular mass less than about 10,000 atomic mass units. The small molecule may be a triazole pesticide.

The protective coating may be between about 10 μm and about 40 μm thick.

In another aspect, there is provided a process for coating a solid phase microextraction (SPME) fibre with a protective coating which has a surface that is substantially uniform and substantially smooth. The process includes: coating the SPME fibre with a protective coating pre-polymer; passing the protective coating pre-polymer coated SPME fibre though an aperature of predetermined size to remove excess protective coating pre-polymer; and curing the protective coating pre-polymer coated SPME fibre to form a protective coating coated SPME fibre.

The substantially uniform, substantially smooth surface may have, on average: fewer than 2 imperfections greater than 10 nm in length per 1000 $nm^2$ of protective coating, as seen on a 900× magnification of an Electron Scanning Microscope, fewer than 1 imperfections greater than 10 nm in length per 1000 $nm^2$ of protective coating, as seen on a 900× magnification of an Electron Scanning Microscope, or fewer than 0.1 imperfections greater than 10 nm in length per 1000 $nm^2$ of protective coating, as seen on a 900× magnification of an Electron Scanning Microscope. In some examples, the substantially uniform, substantially smooth surface may have no observable defects when viewed at 900× magnification using an Electron Scanning Microscope.

The process may further include repeating the coating, passing and curing steps to further coat the protective coating coated SPME fibre with another layer of a protective coating.

The protective coating may include polydimethylsiloxane (PDMS) and curing the PDMS pre-polymer coated SPME fibre may include heating the PDMS pre-polymer coated SPME fibre under vacuum in an inert environment. For example, the PDMS pre-polymer coated SPME fibre may be heated to 50° C. under $N_2$ for 12 hours.

The protective coating may be between about 10 μm and about 40 μm thick.

In yet another aspect, there is provided a method of direct immersion solid phase microextraction (DI-SPME) of a small molecule from a food matrix that includes carbohydrates. The method includes: providing the food matrix; immersing a coated solid phase microextraction (SPME) fibre into the food matrix, removing the coated SPME fibre from the food matrix; and analyzing the small molecule extracted from the food matrix by chromatography, where the coated SPME fibre includes: a SPME fibre for absorbing the small molecule from the food matrix; and a protective coating which has a surface that is substantially uniform and substantially smooth, the protective coating reducing adsorption of the carbohydrates onto the SPME fibre and allowing the SPME fibre to extract the small molecule from the food matrix;

The chromatography may be gas chromatography.

The protective coating may include polydimethylsiloxane (PDMS) or polyfluorocarbons. The small molecule may be a triazole pesticide.

The food matrix may be selected from the group consisting of fruit pulp, fruit juice, vegetable pulp, vegetable juice, and any combination thereof.

The protective coating may be between about 10 μm and about 40 μm thick.

The substantially uniform, substantially smooth surface may have, on average: fewer than 2 imperfections greater than 10 nm in length per 1000 nm$^2$ of protective coating, as seen on a 900× magnification of an Electron Scanning Microscope, fewer than 1 imperfections greater than 10 nm in length per 1000 nm$^2$ of protective coating, as seen on a 900× magnification of an Electron Scanning Microscope, or fewer than 0.1 imperfections greater than 10 nm in length per 1000 nm$^2$ of protective coating, as seen on a 900× magnification of an Electron Scanning Microscope. In some examples, the substantially uniform, substantially smooth surface may have no observable defects when viewed at 900× magnification using an Electron Scanning Microscope.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1:
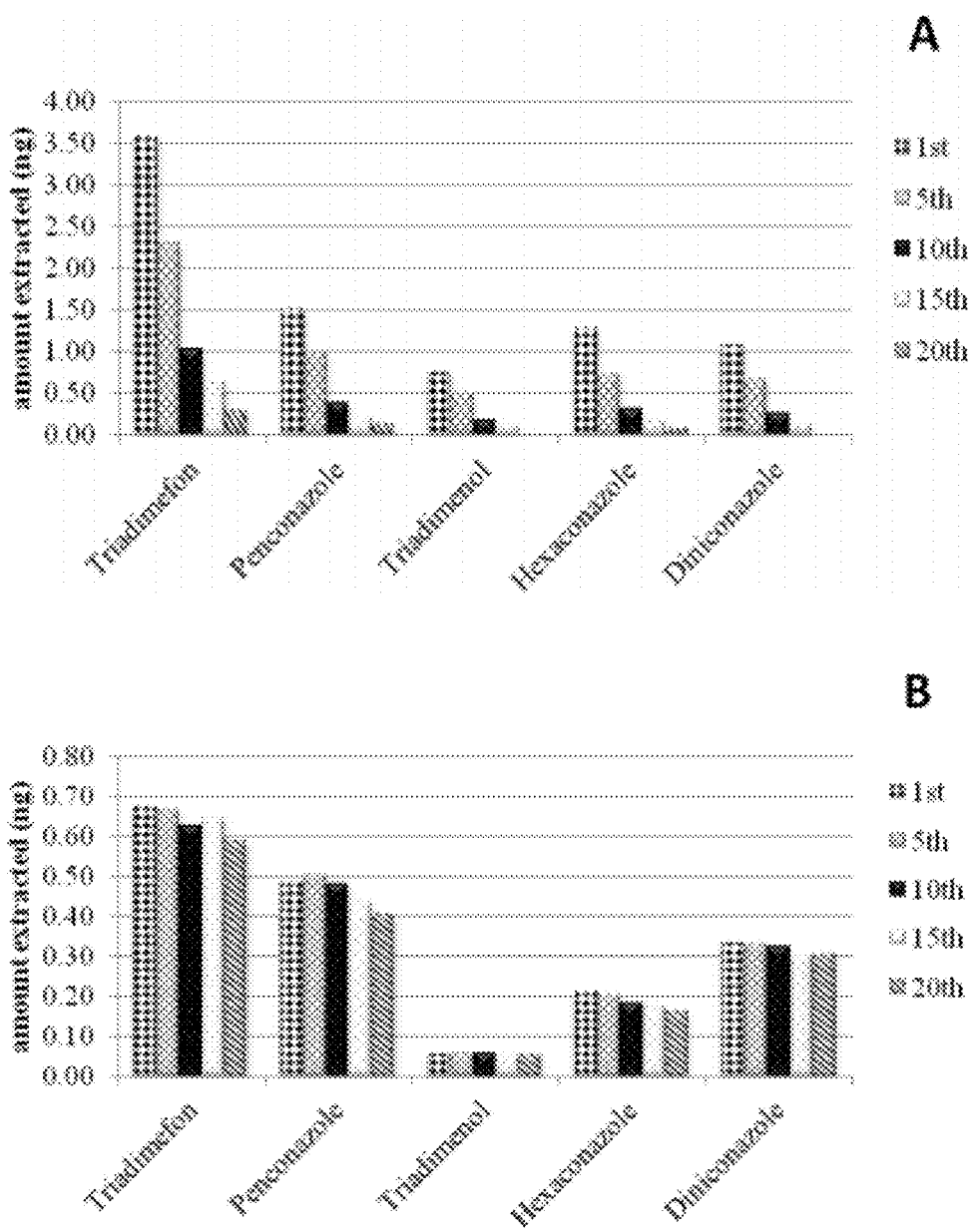
FIG. 1A is a graph which illustrate the repeatability of commercial PDMS/DVB 65 μm fibres in grape matrix.
FIG. 1B is a graph which illustrate the repeatability of commercial PDMS 100 μm fibres in grape matrix.

The appropriate selection of a fibre coating in solid phase microextraction (SPME) is one of the most critical steps in SPME method development. The suitability of the fibre coating for a specific analyte of interest is determined by the polarity of the coating and its selectivity towards the analytes in contrast to other matrix components. However, currently only a limited number of different fibre coatings are commercially available, thus, limiting the application of SPME for the determination of pesticides residues from various matrices.

Generally, the present disclosure provides SPME fibres which are protectively coated with a coating that does not adsorb carbohydrates and which is stable to chromatographic techniques used to analyze the extracted small molecules. Non-limiting examples of such a protective coating include polydimethylsiloxane (PDMS) and polyfluorocarbons. Examples of chromatographic techniques include gas chromatography (GC), which may operate at a temperature greater than 100° C., for example 250° C.

The protective coating has a surface that is substantially uniform and substantially smooth. In some examples, the surface is substantially non-porous.

In the context of the present application, the term "substantially" would be understood to mean "nearly completely". For example, a surface which is "substantially uniform" would be understood to mean a surface which is "almost completely uniform", but which may include insignificant amounts of non-uniformity. Insignificant amounts of non-uniformity would be understood to mean that the surface may have variations in uniformity, but that those variations do not result in adsorption of sufficient amount of carbohydrates to foul the SPME fibre. Similarly, a surface which is "substantially smooth" would be understood to mean "nearly completely smooth", but which may include an insignificant numbers of bumps, depressions or both. Insignificant numbers of bumps, depressions or both would be understood to mean that the surface may have bumps, depressions or both, but that those bumps, depressions or both do not result in adsorption of sufficient amount of carbohydrates to foul the SPME fibre. The term "substantially non-porous" would be understood to mean that the surface is "almost completely" free from pores that would adsorb carbohydrates and foul the SPME fibre. A "substantially non-porous" surface would not be considered impermeable as the surface would still allow small molecules to be extracted from the matrix into the SPME fibre.

Such a substantially uniform, substantially smooth surface would be understood to have, for example, on average fewer than 2 imperfections greater than 10 nm in length per 1000 nm$^2$ of protective coating, as seen on a 900× magnification of an Electron Scanning Microscope (ESM). In some examples, the protective coating may have, on average, fewer than 1 imperfection greater than 10 nm in length per 1000 nm$^2$ of protective coating, as seen on a 900× magnification of an Electron Scanning Microscope (ESM). In some examples, the protective coating may have, on average, fewer than 0.1 imperfection greater than 10 nm in length per 1000 nm$^2$ of protective coating, as seen on a 900× magnification of an Electron Scanning Microscope (ESM). In other examples, the substantially uniform, substantially smooth surface may have no observable defects when viewed at 900× magnification using an Electron Scanning Microscope. In preferred examples, the protective coating, when viewed at 900× magnification, has a surface that looks substantially like the surface of the coating shown in FIG. 3A. In the context of the present application, a surface which looks "substantially like" another surface would be understood to mean that if photographs of both surfaces were taken under similar conditions, the two surfaces would be of similar uniformity and smoothness.

Accordingly, the disclosure provides a coated solid phase microextraction (SPME) fibre for use in direct immersion SPME of a food matrix that includes carbohydrates, the coated SPME fibre includes: a SPME fibre for absorbing small molecules from the food matrix; and a protective coating which has a surface that is substantially uniform and substantially smooth, the protective coating reducing adsorption of the carbohydrates onto the SPME fibre and allowing the SPME fibre to extract the small molecules from the food matrix.

In one aspect, the present disclosure provides a commercial SPME fibre coated with a thin layer of PDMS to create a new PDMS coated SPME fibre. The SPME fibres may be used for DI-SPME. This PDMS coated SPME fibre may be compatible with food matrixes that include carbohydrates, while retaining the SPME fibre's original coating sensitivity towards the analytes of interest.

PDMS, as a liquid coating, suffers less from irreversible fouling effect caused by matrix components compared to solid coatings. The matrix components which may cause fouling include, for example, carbohydrates, such as mono-, di-, and poly-saccharides, and proteins present in the matrix. PDMS may be used regardless of the sensitivity of the coating towards the analytes of interest. PDMS is also stable to elevated temperatures and is, therefore, stable to chromatographic techniques such as gas chromatography, which may be used to analyze pesticides.

The sorptive properties of the PDMS may not be affected by fouling by non-volatile matrix macromolecules, such as carbohydrates. Consequently, it is believed that PDMS is suitable for DI-SPME sampling of highly complex matrices that include carbohydrates. If fouling of the PDMS occurs in highly complex matrices, a physical cleaning of the polymer may be sufficient to return the PDMS coated fibres to operational status.

As discussed in the examples, below, grapes were chosen as a model of a complex matrix that includes carbohydrates. Triazoles pesticides, which are applied in vineyards, were chosen as model analytes due to their low volatility. The PDMS coated SPME fibre was tested for extraction efficiency and robustness when directly subjected to the grape matrix.

In one example, the PDMS coated SPME fibre is a commercially available PDMS/DVB SPME fibre which is protectively coated by PDMS. As illustrated in the examples, the extraction capabilities of the PDMS coated PDMS/DVB fibre are similar to those exhibited by the original commercial PDMS/DVB coating. It suggests that the PDMS layer has not substantially changed the kinetic and thermodynamic parameters associated to the original coating. The results show that the PDMS coating provides enhanced robustness in highly complex food matrix, such as grapes, when compared to the original commercially available PDMS/DVB.

One aspect of the disclosure relates to coatings which can be used for direct microextraction of small molecules from a vegetable, fruit or other food matrix, such as fruit juice. The small molecules can be drugs or chemicals such as pesticides. The small molecules can be hydrophobic or hydrophilic and should generally weigh less than 10,000 atomic mass units.

The coated SPME fibres can be prepared by covering commercial SPME fibres with PDMS. Examples of commercial SPME fibres which may be used include PDMS/DVB 65 µm, DVB/Carboxen/PDMS 50/30 µm, Carboxen/PDMS 75 µm, and Polyacrylate.

Alternatively, the coatings can be prepared by covering flexible fibres with a suspension of various extractive particles (for example: divinylbenzene, C-18/silica, RP-amide/silica, or HS-F5/silica) in a bonding polymer (for example: PDMS, polyacrylonitrile (PAN), polyethylene glycol, polypyrrole, derivatised cellulose, polysulfone, or polyamide). The bonding polymer is then covered by polydimethylsiloxane (PDMS).

The bonding polymer may have properties that allow it to reduce adsorption of proteins or macromolecules onto the SPME particles, even if such a reduction may not be available when the bonding polymer is covered by PDMS.

C-18/silica particles would be understood by one of skill in the art to comprise silica particles derivatized with a hydrophobic phase, the hydrophobic bonded phase comprising octadecyl. For RP-amide-silica particles, the bonded phase comprises palmitamido-propyl. For HS-F5-silica particles, the bonded phase comprises pentafluorophenyl-propyl. The particles can be about 1.7 to about 50 µm particles. Preferably, the particles can be about 2 to about 20 µm particles. Preferably, the particles can be about 3 to about 10 µm particles. More preferably, the particles can be about 3 to about 7 µm particles. The particles can be spherical. The pore size diameter can be about 10 to about 200 Å. Preferably, the pore size can be about 100 to about 180 Å. The surface area can be about 200 m$^2$/g to about 800 m$^2$/g. Preferably, the surface area can be about 200 m$^2$/g to about 300 m$^2$/g.

It would be understood by a person of skill in the art that appropriate coatings can be formed with other extractive particles, and particularly with any extractive particles currently used in solid phase extraction or affinity chromatography (e.g. high pressure liquid chromatography), depending on the nature of the compound being extracted, in a similar manner than affinity chromatography relies on different particles for separating various compounds. For example, other particles could include such particles as: normal-phase silica, C1/silica, C4/silica, C6/silica, C8/silica, C30/silica, phenyl/silica, cyano/silica, diol/silica, ionic liquid/silica, molecular imprinted polymer particles, or carboxen 1006. Mixtures of particles can also be used in the coatings. The particles can be inorganic (e.g. silica), organic (e.g. carboxen or divinylbenzene) or inorganic/organic hybrid (e.g. silica and organic polymer). Furthermore, a person of skill in the art would understand that other polymers could be used as glue or support so long as the bonding polymer is covered by a coating of PDMS.

It would be readily understood by one of skill in the art that the diameter of a fibre for SPME can be of millimeter to nanometer dimensions. Preferably, the diameter of a fibre can be between 0.1 millimeters and 0.6 millimeters. More preferably, the diameter of a fibre can be about 0.13 millimeters (0.005 inches). The wire can be formed of any acceptable material that would be amenable for use in a biological matrix. Such material may include silica, plastic, carbon or metal wire. Metal wires may be stainless steel, titanium, a nickel-titanium alloy, or any other metal wire known to a person of skill in the art. The flexible, inert, biocompatible nickel-titanium alloy can be Nitinol. A metal with shape memory properties that enable the wire to maintain straightness, even after it is coiled, can be desirable.

Coated SPME wires can be used for in vitro analysis of chemical concentrations in a food matrix. Coated SPME probes can have any combination of extractive particles bonded with an bonding polymer, such as PDMS, polyacrylonitrile (PAN), polyethylene glycol, polypyrrole, derivatised cellulose, polysulfone, or polyamide solution. In order to reduce fouling by carbohydrates in the food matrix, the bonding polymer is then covered by polydimethylsiloxane (PDMS).

A non-limiting example of the coating includes: a PDMS/DVB coating. Other non-limiting examples of the coating include: a PAN/C-18 coating, a PAN/RP-amide coating, a polyethylene glycol/HS-F5 coating, a derivatised cellulose/C-18 coating, a polypyrrole/C-30 coating, a polysulfone/phenyl coating and polyamide/cyano coating where the bonded extractive particles are then covered with a protective coating of PDMS.

Another aspect of the disclosure relates to a continuous-coating process for producing SPME fibres covered with a coating which is compatible with a carbohydrate-containing matrix. Preferably, the bonding polymer is PDMS and the extractive particles are DVB.

In one example of the continuous-coating process, a fibre can be wound on a spool and can be threaded through an applicator with a fixed opening that contains a suspension of extraction particles in a solution of bonding polymer. The extraction particles can be DVB, C-18, RP-amide, HS-F5 silica particles or any other particle listed above. Mixtures of particles can be used. When the particles are silica particles and the bonding polymer is PAN, the ratio of PAN/silica can be between 0.3 and 0.7 wt/wt. The preferred ratio of PAN/silica is 0.5 wt/wt. The ratio is based on the bare weight of silica and adjusted to the phase loading on the silica particles. The PAN/solvent solution can be between 5% and 15% PAN (w/w). Preferably, the PAN/solvent solution is between about 7.5% and about 12% PAN (w/w). More preferably, the PAN/solvent solution is about 10% PAN/solvent (w/w). The solvent can be any solvent known to one of skill in the art that dissolves PAN, for example: dimethylformamide (DMF), dimethyl sulfoxide, NaSCN, $Ca(CNS)_2$, nitric acid, ethylene carbonate or mixtures thereof. More preferably, the solvent can be DMF. The suspension can be coated on a length of flexible metal fibre. The coated fibre can be passed through a heater at an elevated temperature and connected to another reel driven by a motor that can pull the fibre at a fixed speed. The elevated temperature can be between about 150° C. and about 300° C. Preferably, the elevated temperature is between about 180° C. and about 210° C. A person of skill in the art would readily understand that PAN is fully polymerized when it is dissolved in the solvent and as long as the solvent is fully evaporated, the fibre is properly coated. As such, any means known to a person of skill in the art to remove the solvent can be used to dry the coated fibres. Once the fibre is properly coated, the fibre is immersed in a PDMS solution. The PDMS solution may be formed using a commercial silicon elastomer kit, for example SYLGARD® 184 SILICONE ELASTOMER KIT by Dow Corning, which is mixed in a 10:1 PDMS base:curing agent. The PDMS solution may be subjected to centrifugation for 3 min at 4000 rpm for degassing. Once the fibre is immersed in the PDMS solution, the fibre is subsequently pulled out at a slow rate and passed through a Teflon piece of predetermined aperture in order to remove excess polymer and provides a fibre with a thin layer of PDMS coating. The rate at which the fiber was passed through the aperture would depend on the viscosity of the PDMS solution. In some examples, the rate is about 1 cm/min.

After coating the fibre with PDMS, the coated fibre is cured. When using the SYLGARD® 184 kit, the PDMS may be cured by playing the coated fibre in a vacuum oven at 0.1 atmospheres, 50° C. under $N_2$ flow for 12 hrs. Alternative conditions could be used to cure the coated fibre depending on the polymer initiator and monomer used.

The coating/curing process may be repeated multiple times, for example to obtain a coating which is more uniform, more non-porous, and which has a smoother surface. The size of the aperture determines the thickness of the coating. In particular examples, the aperture is chosen to provide a coating which is 10 μm thick. Repeating the coating/curing process a second time would, in some examples, provide a coating which is about 20 μm thick. In preferred embodiments, the thickness of the coating is between about 10 μm and about 40 μm. In particular embodiments, the thickness of the coating is between about 25 μm and about 30 μm.

Prior to use, the fibre may be conditioned in a GC injection port (PTV) under helium flow from 100° C. (hold for 5 min) to 250° C. (hold for 30 min) at 5° C./min. The fibre may additionally be conditioned again at 250° C. for 10 min. The 10-min conditioning cycle may be repeated a few more times until a stable GC baseline was obtained.

In another example of a continuous-coating process, the fibre is a commercial SPME fibre, such as a PDMS/DVB fibre. The fibre can be wound on a spool and can be threaded through an applicator with a fixed opening that contains a PDMS solution. The PDMS solution may be formed using a commercial silicon elastomer kit, for example SYLGARD® 184 SILICONE ELASTOMER KIT by Dow Corning, which is mixed in a 10:1 PDMS base:curing agent. The PDMS solution may be subjected to centrifugation for 3 min at 4000 rpm for degassing. Once the fibre is immersed in the PDMS solution, the fibre is subsequently pulled out at a slow rate and passed through a Teflon piece of predetermined aperture in order to remove excess polymer and provides a fibre with a thin layer of PDMS coating. After coating the fibre with PDMS, the coated fibre is cured. When using the SYLGARD® 184 kit, the PDMS may be cured by playing the coated fibre in a vacuum oven at 50° C. under $N_2$ flow for 12 hrs. The coating/curing process may be repeated multiple times, for example to obtain more complete and uniform coverage. Prior to use, the fibre may be conditioned in a GC injection port (PTV) under helium flow from 100° C. (hold for 5 min) to 250° C. (hold for 30 min) at 5° C./min. The fibre may additionally be conditioned again at 250° C. for 10 min. The 10-min conditioning cycle may be repeated a few more times until a stable GC baseline was obtained.

Another aspect of the disclosure relates to a dip-coating process for producing SPME fibres covered with a coating which is compatible with a carbohydrate-containing matrix. Preferably, the bonding polymer is PDMS and the extractive particles are DVB. A dip-coating process would be understood by a person of skill in the art to be a batch process.

In one example of the dip-coating process, the fibre is a commercial SPME fibre, such as a PDMS/DVB fibre. The PDMS/DVB fibre is immersed in a PDMS solution. The PDMS solution may be formed using a commercial silicon elastomer kit, for example SYLGARD® 184 SILICONE ELASTOMER KIT by Dow Corning, which is mixed in a 10:1 PDMS base:curing agent. The PDMS solution may be subjected to centrifugation for 3 min at 4000 rpm for degassing. Once the fibre is immersed in the PDMS solution, the fibre is subsequently pulled out at a slow rate and passed through a Teflon piece of predetermined aperture in order to remove excess polymer and provides a fibre with a thin layer of PDMS coating. The rate at which the fiber was passed through the aperture would depend on the viscosity of the PDMS solution. In some examples, the rate is about 1 cm/min.

After coating the fibre with PDMS, the coated fibre is cured. When using the SYLGARD® 184 kit, the PDMS may be cured by playing the coated fibre in a vacuum oven at 50° C. under $N_2$ flow for 12 hrs.

The coating/curing process may be repeated multiple times, for example to obtain a coating which is more uniform, more non-porous, and which has a smoother surface. The size of the aperture determines the thickness of the coating. In particular examples, the aperture is chosen to provide a coating which is 10 μm thick. Repeating the coating/curing process a second time would, in some examples, provide a coating which is about 20 μm thick. In preferred embodiments, the thickness of the coating is between about 10 μm and about 40 μm. In particular embodiments, the thickness of the coating is between about 25 μm and about 30 μm.

In examples where the SPME fibres are made using extraction particles and a bonding polymer, the wires can be pre-processed before the coating process in order to clean and roughen the surface. Pre-processing can be accomplished by washing with acetone, etching for 1 min in concentrated hydrochloric acid, washing the wire with water and/or thoroughly cleaning the wire by sonication in water. Prior to use, the coated fibres can be conditioned in a water:methanol 50:50 wash for 30 min. Conditioning the C-18 based coatings with water or higher proportion of methanol can lead to worse reproducibility. Other coatings, however, can require only a very brief conditioning step (less than 5 min), or even none at all.

EXAMPLE 1

Preparation of Drape Matrixes with Triazole Compounds and Extraction with Commercial SPME Fibres Different types of commercial SPME fibres were evaluated using DI-SPME and HS-SPME modes in order to ensure the best extraction efficiency for all triazole pesticides. Specifically, PDMS 100 μm, PDMS/DVB 65 μm, DVB/Car/PDMS 50/30 μm, Car/PDMS 75 μm and PA 85 μm, were compared in terms of extraction efficiency, while extraction (30 min) and desorption times (7 min), and sample temperature (30° C.) were kept constant.

Conventionally, HS-SPME mode is used for the extraction of analytes from complex samples in order to protect the fibre coating from damage by high molecular mass and other non-volatile interferences present in the sample matrix. Conversely, DI-SPME mode is used for the extraction of compounds with low-to-medium volatility. The different commercial SPME fibres were tested using a sample that includes highly complex matrix (grapes) and analytes of low volatility, as seen in Table 1. Both HS-SPME and DI-SPME were tested.

TABLE 1

| Analyte | Mol. Wt. (g/mol) | Sol. in water (mg/L) | LogP (at pH 7, 20° C.) | Vapour Pressure (at 25° C., mPa) | Henry's Law Constant (Pa * m³/mol) |
|---|---|---|---|---|---|
| triadimefon | 293.8 | 70 | 3.18 | 0.02 | 9E−5 |
| penconazole | 284.18 | 73 | 3.72 | 0.366 | 6.6E−4 |
| triadimenol | 295.76 | 72 | 3.18 | 0.0005 | 3.5E−6 |
| hexaconazole | 314.21 | 18 | 3.9 | 0.018 | 3.33E−4 |
| diniconazole | 326.2 | 4 | 4.3 | 2.96 | 4E−2 |

For the evaluation of the commercial SPME fibres, uncontaminated white grapes, purchased at local market in Waterloo (ON Canada), were manually stemmed, washed with deionized water, dried and crushed using a blender. For HS-SPME extraction mode, a sample aliquot (4 g) was weighed in a 10 mL vial, fortified at 500 μg of triazole pesticides: triadimefon, penconazole, triadimenol, hexaconazole or diniconazole, per gram of aliquot.

Spiked analytes in grape matrix were pre-incubated at room temperature for 60 min prior to extraction to allow for the binding of the analytes-matrix to occur. A 5 min incubation of the sample was performed in the agitation unit at 500 rpm and at 70° C., followed by a 60 min extraction at 70° C., while stirring at 500 rpm. Following extraction, the fibre was placed in the GC injection port for desorption for 7 min at temperatures 10° C. below de maximum operational temperature recommend by the manufacturer. For DI-SPME extraction mode, a sample aliquot (9 g) was weighed in a 10 mL vial, fortified at 100 μg/g. A 5 min incubation of the sample was performed in the agitation unit at 500 rpm and at 30° C., followed by a 30 min extraction at 30° C., while stirring at 500 rpm. Following extraction, the fibre was desorbed using the same above-mentioned conditions.

Tables 2 and 3 show the mean and the standard deviation values obtained for triplicate extractions of triazole pesticides performed on each fibre. Values are reported as mean (%) of extraction±standard deviation (n=3) where "n.d"=not detected.

The extraction of triazole pesticides was much lower with the HS-SPME mode, which indicated that the larger molecular weight and the low Henry's law constants of triazoles caused them to fail to be transported through the barrier of air. Conversely, all compounds had very higher extraction efficiencies with DI-SPME for all the fibre coatings assayed relative to the HS-SPME mode. The best results were obtained using the PDMS/DVB where an approximately 100-fold improvement was observed when using DI-SPME compared to HS-SPME.

It is worth noting that after only three extractions in DI mode, an inspection of the fibres on optical microscope showed dark little spots suggestive of fibre fouling (especially for the solid coatings PDMS/DVB and DVB/Car/PDMS).

TABLE 2

| | Amount Extracted | | | | | |
|---|---|---|---|---|---|---|
| | PDMS/DVB | | DVB/Car/PDMS | | PA | |
| Compound | DI | HS | DI | HS | DI | HS |
| Triadimefon | 15.2 ± 0.8 | 0.20 ± 0.01 | 9.4 ± 0.6 | 0.16 ± 0.01 | 8.2 ± 0.6 | 0.17 ± 0.01 |
| Penconazole | 6.7 ± 0.6 | 0.51 ± 0.07 | 3.0 ± 0.2 | 0.31 ± 0.02 | 4.3 ± 0.4 | 0.45 ± 0.01 |
| Triadimenol | 4.2 ± 0.3 | 0.04 ± 0.01 | 1.4 ± 0.2 | n.d. | 1.2 ± 0.2 | n.d |
| Hexaconazole | 4.8 ± 0.3 | 0.19 ± 0.01 | 1.2 ± 0.2 | 0.1 ± 0.01 | 1.8 ± 0.3 | 0.16 ± 0.01 |
| Diniconazole | 11.1 ± 0.6 | 0.20 ± 0.01 | 4.8 ± 0.2 | n.d. | 2.8 ± 0.4 | 0.17 ± 0.01 |

TABLE 3

| | Amount Extracted | | | |
|---|---|---|---|---|
| | PDMS | | Car/PDMS | |
| Compound | DI | HS | DI | HS |
| Triadimefon | 5.6 ± 0.7 | 0.14 ± 0.01 | 2.0 ± 0.5 | n.d |
| Penconazole | 4.6 ± 0.2 | 0.38 ± 0.03 | 0.40 ± 0.09 | n.d |
| Triadimenol | 0.4 ± 0.2 | n.d. | 0.20 ± 0.08 | n.d |
| Hexaconazole | 1.2 ± 0.2 | 0.14 ± 0.01 | 0.30 ± 0.02 | n.d |
| Diniconazole | 1.5 ± 0.2 | 0.10 ± 0.01 | 1.9 ± 0.5 | n.d |

Fibre fouling, for example by adsorbed carbohydrates, is one of the most commonly encountered problems with existing commercial SPME coatings applied to direct extraction in food matrices. Adsorbed carbohydrates may be transformed into carbon deposits when heated in analytical instruments, such when used for gas chromatography. Fibre fouling can be very problematic as it can change the chemistry of the coating, hence, affecting the uptake of the analyte, the reproducibility of extraction, resulting in reduced accuracy and decreasing extraction efficiency of the fibre upon repeated use.

EXAMPLE 2

Rinsing SPME Fibres to Reduce Fouling

In an attempt to overcome the problem of fibre fouling by carbohydrates, a rapid rinsing of the fibre in de-ionized water after extraction and prior to desorption was evaluated. Nine mL of nanopure water spiked with triazole pesticides was submitted to DI-SPME using PDMS/DVB fibre (all other extraction parameters kept the same). Rinsing times varying from 20 s to 60 s were tested and compared to extractions without fibre rinsing in order to account for any substantial analyte loss. It was observed that no significant loss of analyte occurs up to 50 s rinsing, thus, it was chosen for further experiments. Subsequently, grape samples were prepared as discussed above and were subjected to extraction applying a 50 sec rinsing prior to desorption and washing and cleaning/conditioning after desorption as previously mentioned. Overall, the obtained results demonstrate an ineffectual improvement in the fibre lifetime. After 20 extraction/desorption cycles in grape matrix the PDMS/DVB fibre was blackened and a substantial decrease in extraction efficiency was observed, resulting in irreproducible results. After 10 extractions, the extraction efficiency had decreased by 33-41% and by the 20th extraction, the efficiency had dropped by 83-89%.

The same experimental set up was repeated for PDMS fibre to evaluate the performance of PDMS coating to determine if PDMS can be used with complex matrix without changes in its sorptive properties for complex lipid-rich matrix and hydrophobic compounds. The results obtained for both sets of experiments are shown in FIG. 1, which illustrates the repeatability of commercial fibres in grape matrix, as represented by amount of analyte extracted after multiple extraction-desorption cycles where FIG. 1A shows the results for PDMS/DVB 65 μm and FIG. 1B shows the results for PDMS 100 μm.

The results for PDMS coating show that, after 10 extractions, the extraction efficiency had decreased by 1-14% and by the 20th extraction, the efficiency had dropped by 2-24%. Accordingly, PDMS coatings offer higher repeatability and robustness to directly extract from complex matrix. PDMS coatings are, therefore, a preferred coating for such applications despite of its low sensitivity towards analytes of high molecular weight.

EXAMPLE 3

A PDMS Coating on an SPME Fibre

It was surprisingly determined that the benefits of a PDMS coating could be obtained together with the benefits of the high sensitivity exhibits by a SPME fibre (for example a PDMS/DVB fibre) by coating the SPME fibre with a PDMS coating.

It was necessary to evaluate the coating method (e.g. spraying or dipping) and the overall parameters, such as addition of solvent, rate of pulling and aperture diameter. The spraying method resulted in coatings which were highly irregular, thus, the work proceeded using dip-coating.

According a preferred example, dip-coating is performed using PDMS pre-polymer and curing agent which were mixed at 10:1 ratio, according to the manufacturer's manual, into a polypropylene centrifuge tube and subjected to centrifugation for 3 min at 4000 rpm for degassing. The coating procedure consisted of immersing the commercial PDMS/DVB fibre into the PDMS solution and subsequently pulling out at a slow rate. Passing it through a Teflon piece of predetermined aperture ensured that a thinner layer was formed, with the excess polymer being removed. After the coating process the coated fibre was placed in a vacuum oven at 50° C. under $N_2$ flow for 12 hrs. The coating/curing process was repeated twice to assure complete and uniform coverage. Prior to use the fibre was conditioned in a GC injection port (PTV) under helium flow from 100° C. (hold for 5 min) to 250° C. (hold for 30 min) at 5° C./min. The fibre was then conditioned again at 250° C. for 10 min. The 10-min conditioning cycle was repeated a few more times until a stable GC baseline was obtained.

In specific embodiments, the PDMS outer layer is obtained using two layers of PDMS, which results in a favorable surface coverage of the original PDMS/DVP coating. Thin coatings (for example coatings made with 1 layer of PDMS and less than 10 μm thick) may have uneven total surface coverage and a coating that still exhibited porous surface. Thick coating (for example coatings made with 3 layers of PDMS and greater than 40 µm thick) may have non-uniform surface coverage in terms of thickness throughout the coating length and/or may have weaker physical stability due to excessive thickness that could led to stripping of the coating when withdrawn inside the fibre needle.

Figure 2A:
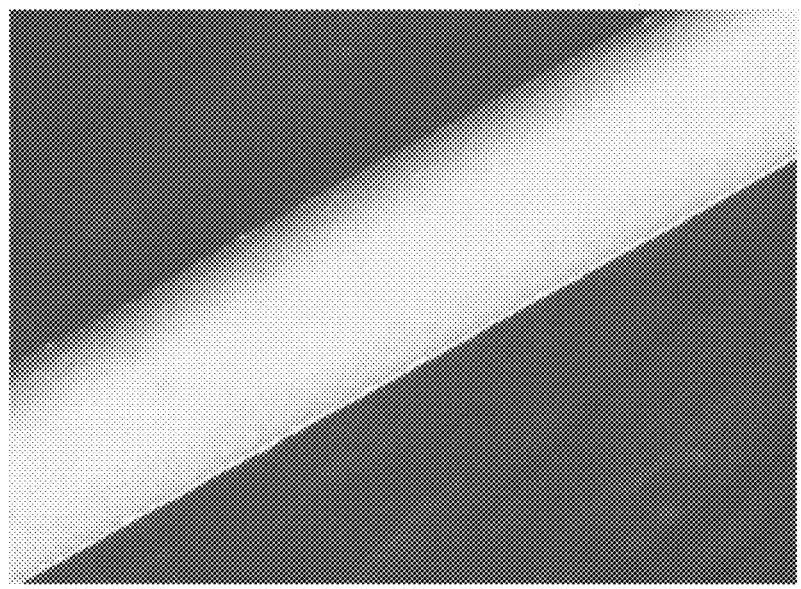
FIG. 2A is a microphotograph of a commercially available PDMS/DVB fibre.
Figure 2B:
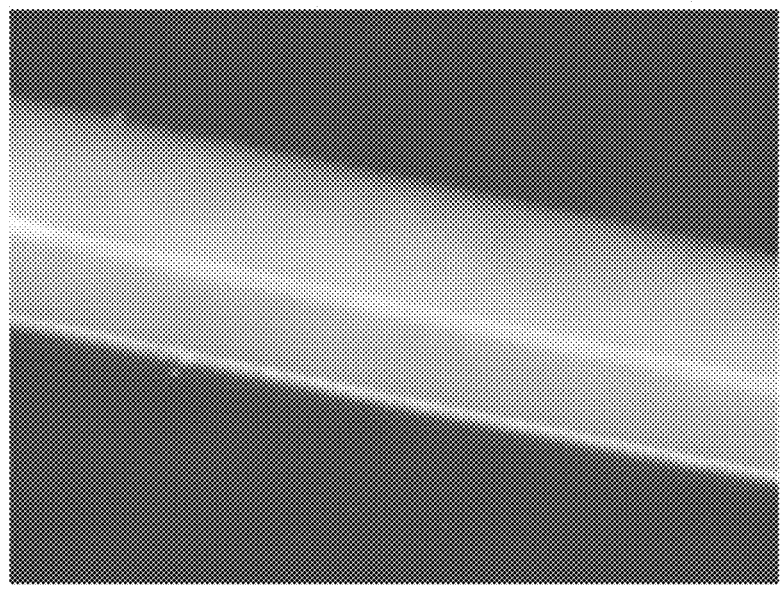
FIG. 2B is a microphotograph of a PDMS coated SPME fibre according to one aspect of the disclosure.

After curing and conditioning, the PDMS coated fibres were inspected using electronic microscope to ensure that a thin layer of smooth surface was achieved. Electronic microphotographs of the PDMS/DVB fibre before and after adding the PDMS external layer is shown in FIG. 2 which shows microphotographs of a PDMS/DVB fibre: (A) as commercially available; and (B) the same fibre coated with an external PDMS layer.

Figure 3A:
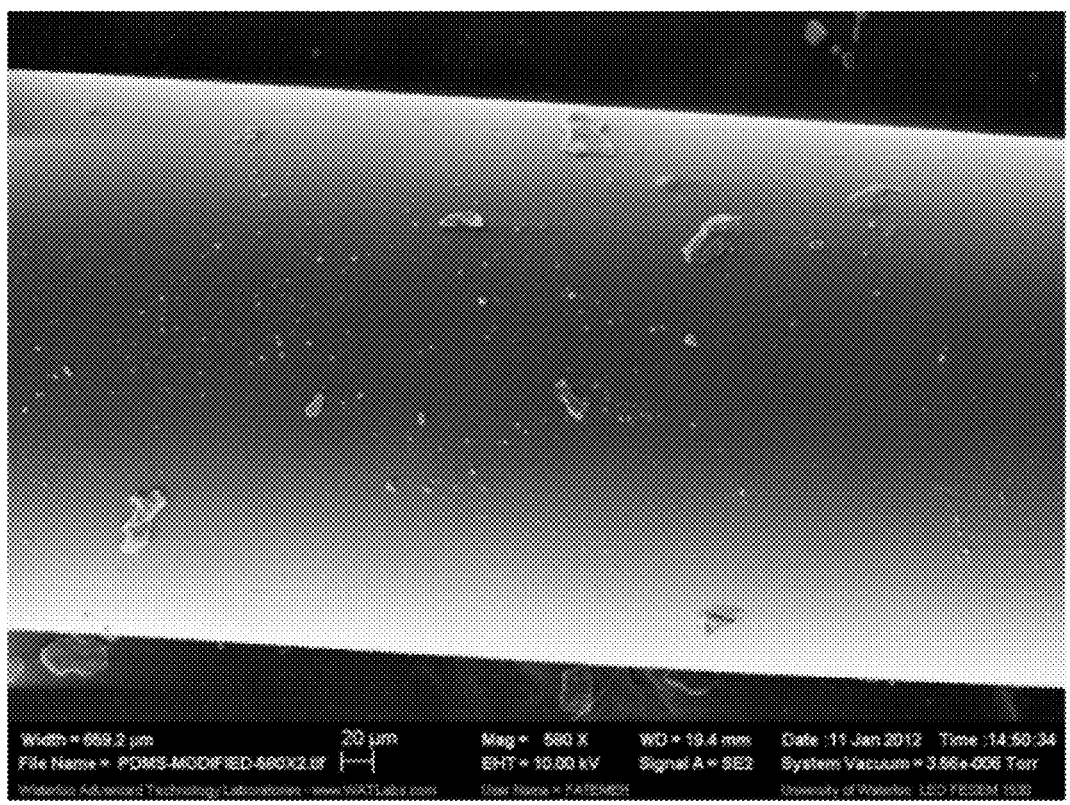
FIG. 3A is a scanning electron microsopy (SEM) image at 580× magnification of a PDMS coated SPME fibre according to one aspect of the disclosure.
Figure 3B:
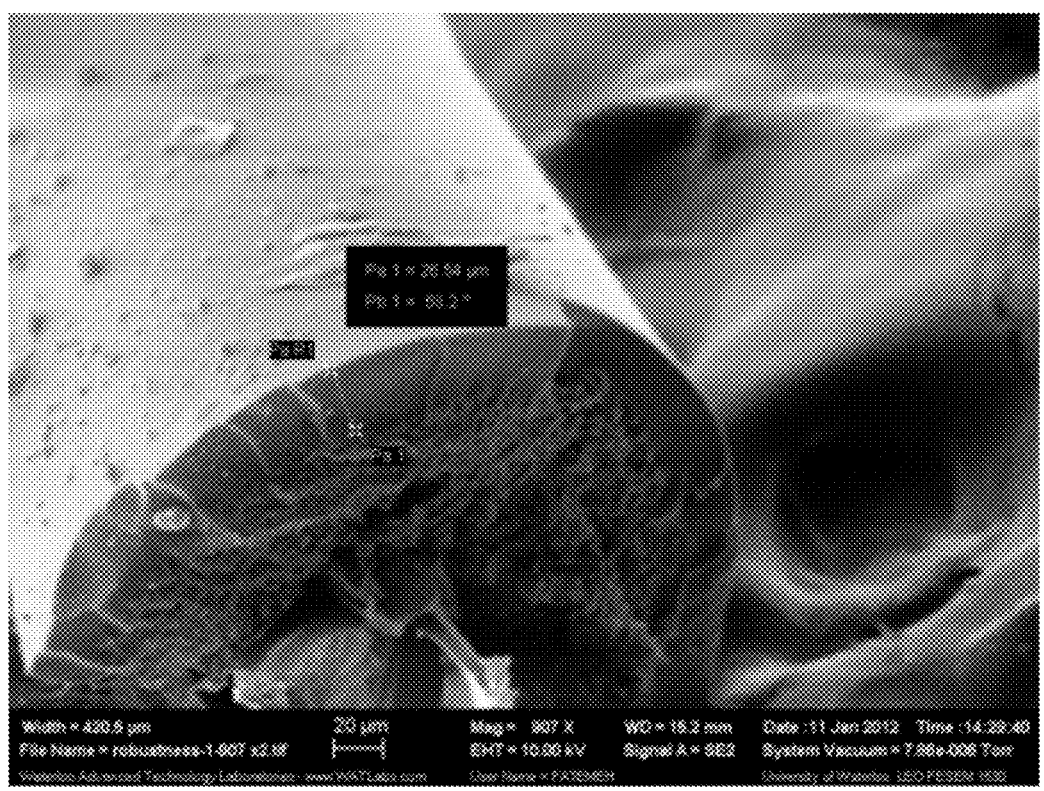
FIG. 3B is an SEM image at 900× magnification of a cross section of a PDMS coated SPME fibre according to one aspect of the disclosure.

As it can be seen, the microphotographs show the formation of a very thin PDMS film on the surface of the PDMS/DVB fibre. The image shows a surface that is substantially uniform and substantially smooth. In order to further verify the topography of the coating surface, as well as the thickness of the PDMS outer layer, scanning electron microscopy (SEM) images were acquired using an LEO 1530 field emission (Carl Zeiss NTS GmbH, Germany). FIGS. 3A and 3B show the SEM images of the coatings (2 layers) after it was covered with a 10 nm layer of gold on its surface where FIG. 3A shows surface morphology using 580× magnification, and FIG. 3B shows estimation of coating thickness using 900× magnification. As it can be seen in FIG. 3B, the estimate PDMS outer layer thickness for the coating was estimated to be around 25-30 µm.

SEM images for coatings prepared using different number of layers of PDMS, as well as surface morphology for non-coated commercial PDMS/DVB fibres are presented in FIG. 3C-3F.

Figure 3C:
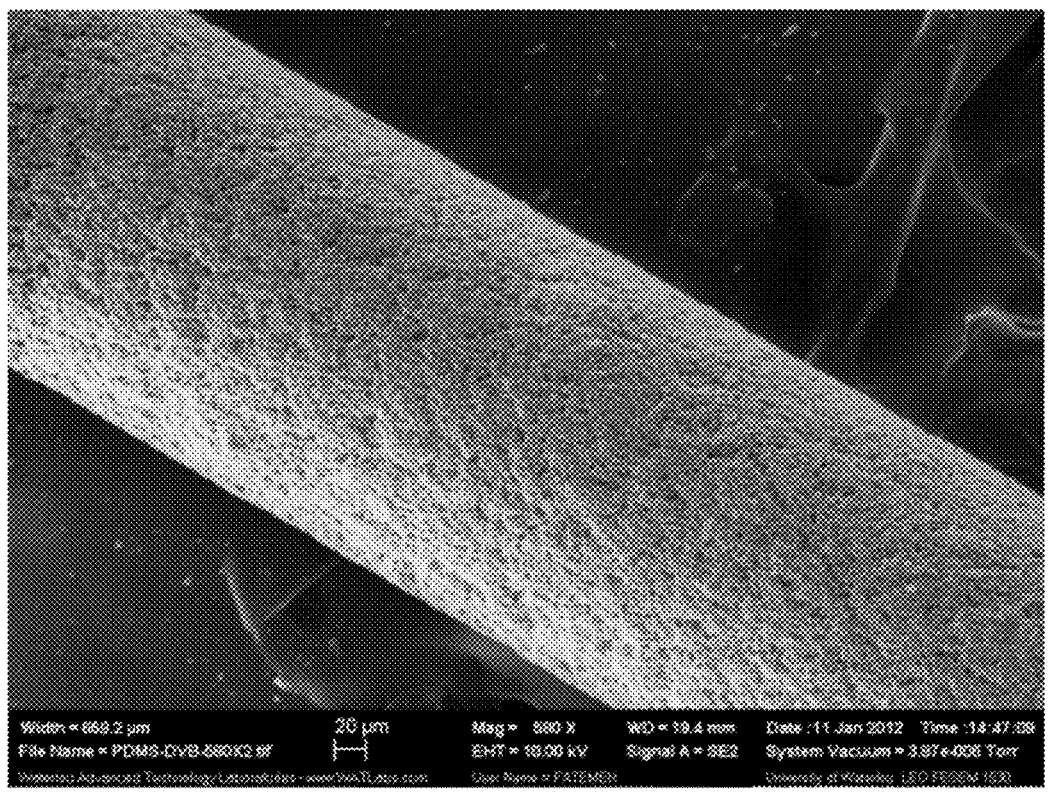
FIG. 3C is an SEM image at 580× magnification of a non-coated commercial PDMS/DVB fibre.
Figure 3D:
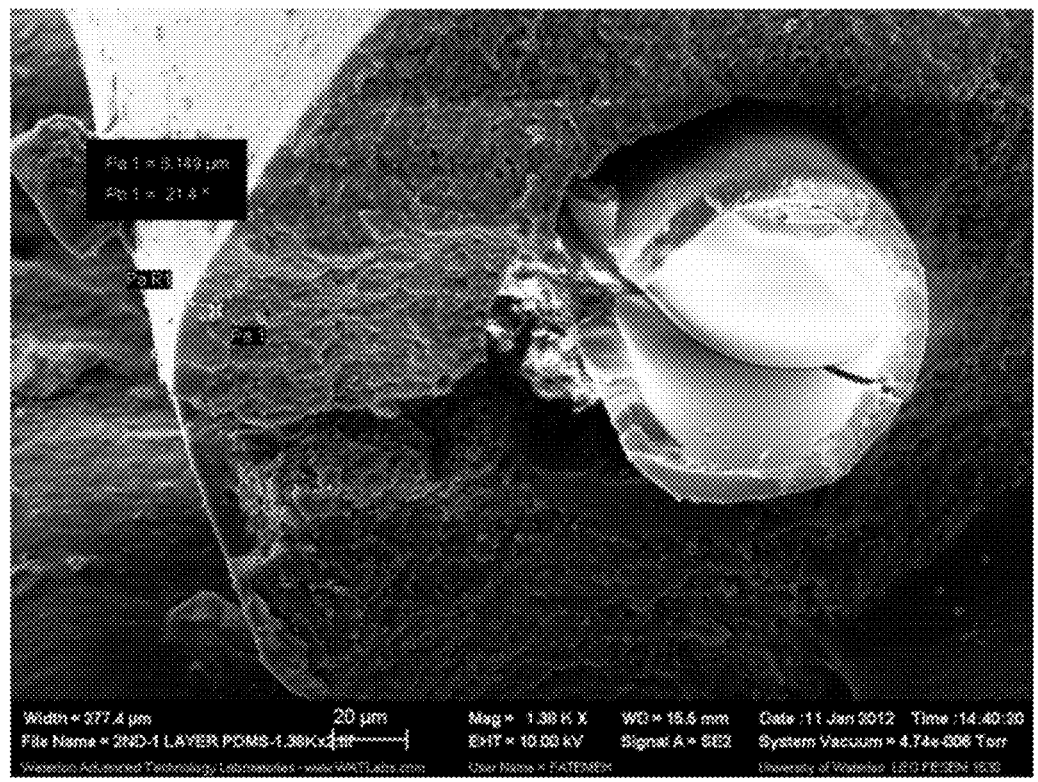
FIG. 3D is an SEM image at about 1400× magnification of a PDMS coated SPME fibre according to one aspect of the disclosure.
Figure 3E:
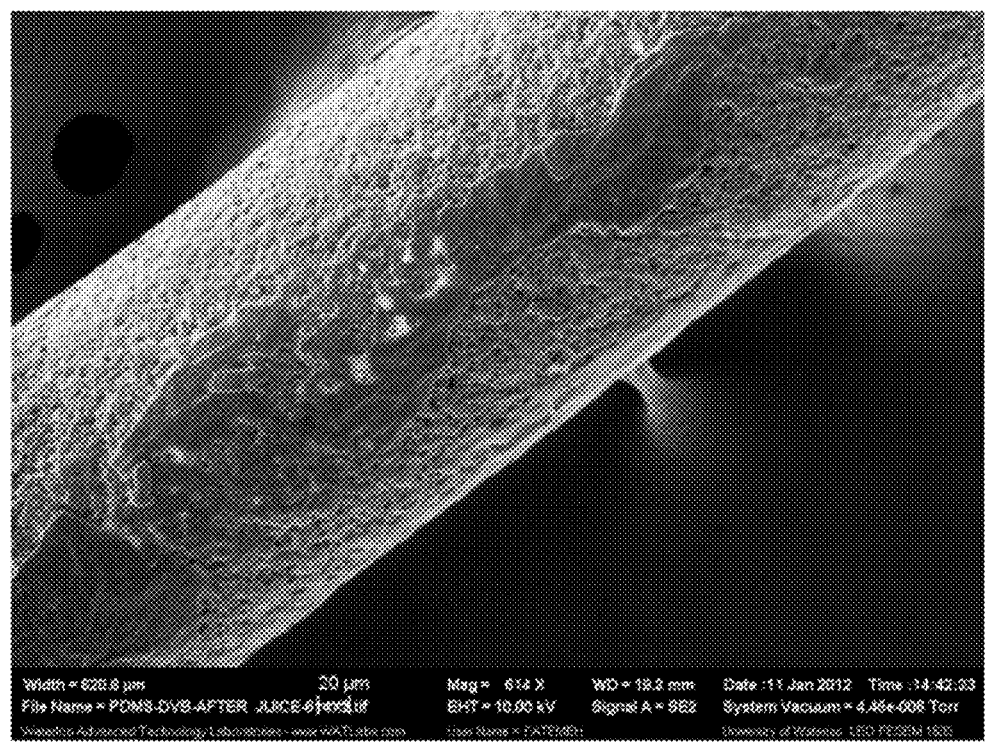
FIG. 3E an SEM image at about 600× magnification of a commercial PDMS/DVB fibre.
Figure 3F:
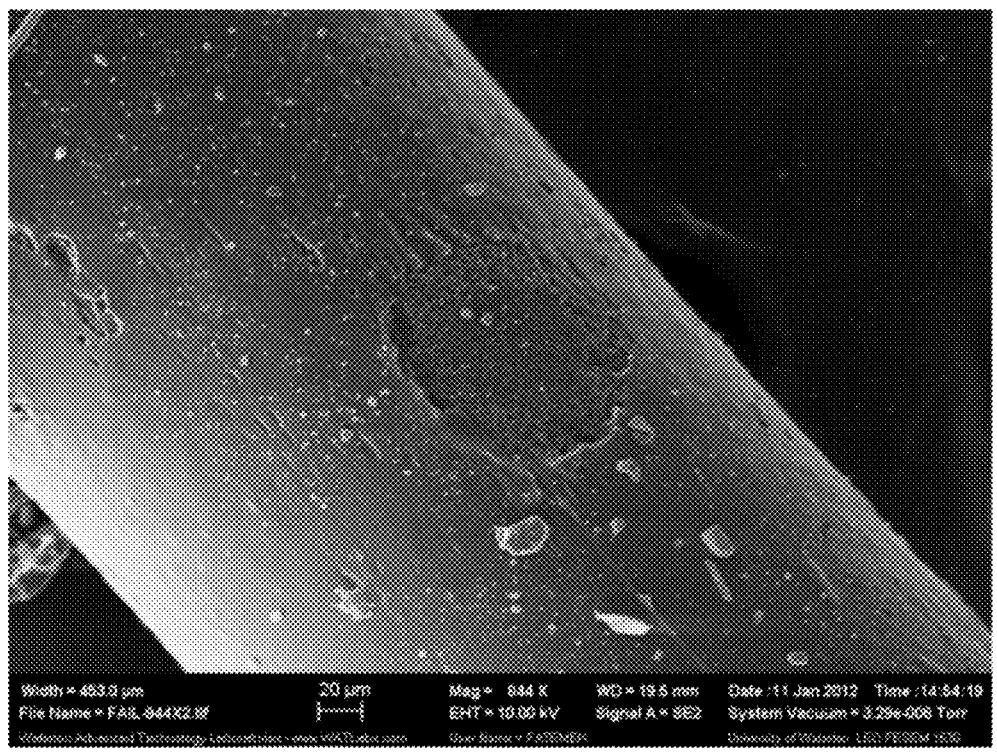
FIG. 3F is an SEM image at about 850× magnification of a PDMS coated PDMS/DVB fibre which does not have a substantially uniform, substantially smooth surface.

FIG. 3C is an SEM image at 580× magnification of a non-coated commercial PDMS/DVB fibre. FIG. 3D is an SEM image at about 1400× magnification of a commercial PDMS/DVB fibre coated with a protective coating having an average thickness of about 10 µm of PDMS. FIG. 3E an SEM image at about 600× magnification of a commercial PDMS/DVB fibre which shows deposits on the fibre after extraction of fruit juice. The deposits are believed to be carbon formed from decomposition of adsorbed carbohydrates at gas chromatography temperatures. If a PDMS coated PDMS/DVB fibre is used that has a surface which is substantially uniform and substantially smooth, the deposits are reduced. In some examples, the deposits do not exist. FIG. 3F is an SEM image at about 850× magnification which shows a PDMS coated PDMS/DVB fibre which does not have a surface which is substantially uniform and substantially smooth. The PDMS coated PDMS/DVB fibre of FIG. 3F would be expected to form carbon deposits after extraction of fruit juice and decomposition of adsorbed carbohydrates at gas chromatography temperatures.

EXAMPLE 4

Evaluation of PDMS Coating on an SPME Fibre

HS-SPME analysis of benzene, toluene, ethylbenzene, and xylenes (BTEX) compounds was used to evaluate the effect of the external PDMS coating layer on extraction capabilities of the PDMS/DVB SPME fibre. This was accomplished by comparing extraction time profiles of the PDMS coated PDMS/DVB with extraction provides obtained using commercial PDMS/DVB 65 µm fibre.

Aqueous solutions containing 100 µg/L of each solute (benzene, toluene, ethylbenzene, or xylenes) was prepared daily. The extractions were performed with the fibre exposed to the headspace of 10 mL vial filled with 3 mL of solution (7 mL of headspace volume). A 5 min pre-extraction equilibration of the sample was performed in the agitation unit at 500 rpm and at 30 C. Varying extraction times, between 15 sec and 20 min, were used. All experiments were performed in triplicate.

It was observed that the slopes of the initial stage of the adsorption profile, were decreased for benzene and had much smaller effect on toluene, ethylbenze and xylene which indicates that the kinetics of extraction for those analytes were influenced by the additional PDMS barrier and this effect was dependent on the magnitude of the analyte characteristic sample-PDMS distribution constant (K). In the PDMS coated PDMS/DVB fibre, the analytes must first diffuse through the PDMS interface prior to the adsorption in the solid DVB coating. Since this in-between phase is a liquid polymer and the analytes have low diffusion coefficients in them, the mass transfer is slowed down and the extraction process is kinetically limited. If the PDMS has lower capacity for a given analyte (i.e. lower K value) than the barrier has higher impact on the mass transfer rate between matrix and the extraction phase.

Figure 4:
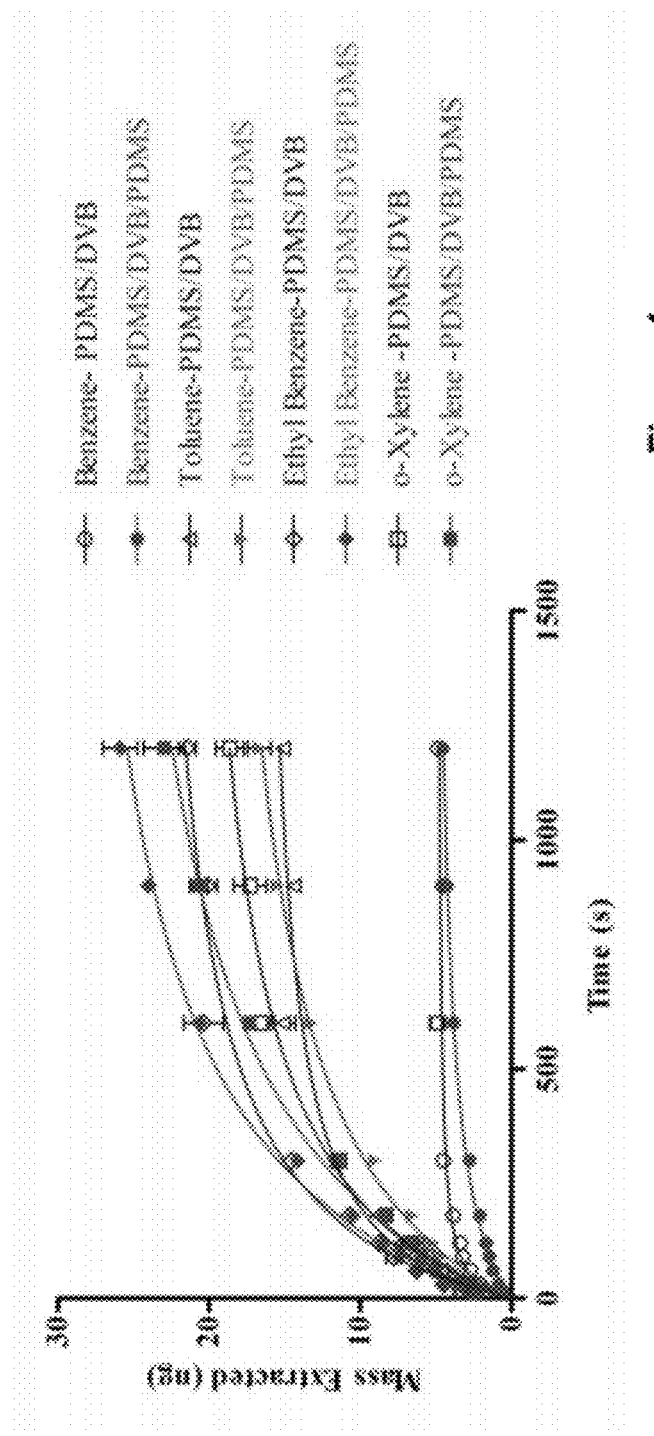
FIG. 4 is a graph which illustrates comparative extraction equilibration for BTEX compounds obtained with the commercial PDMS/DVB and with a PDMS coated SPME fibre according to one aspect of the disclosure.
Figure 5A:
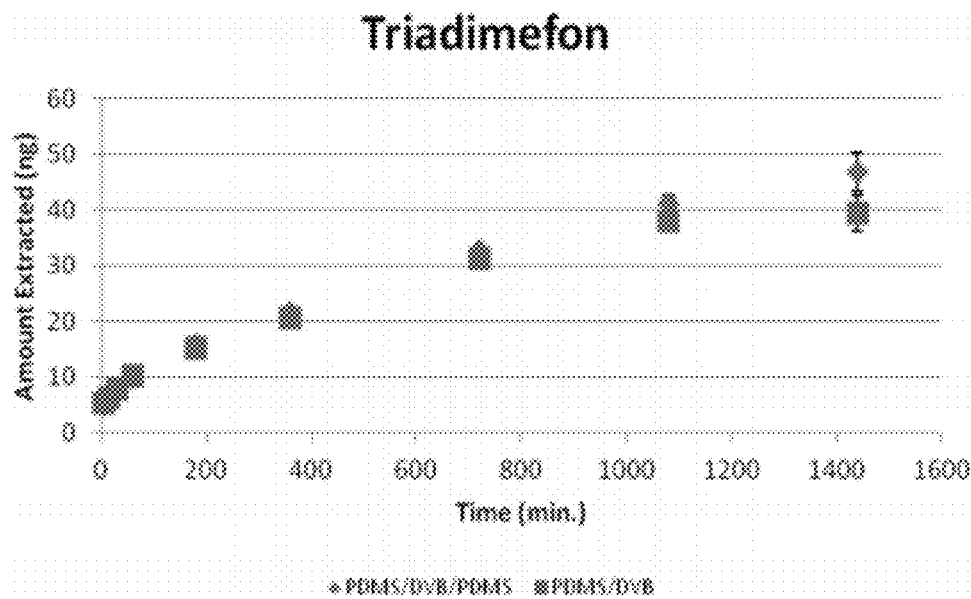
FIGS. 5A-5E are graphs which illustrate comparative extraction equilibration for triazole compounds obtained with the commercial PDMS/DVB and with a PDMS coated SPME fibre according to one aspect of the disclosure.
Figure 5B:
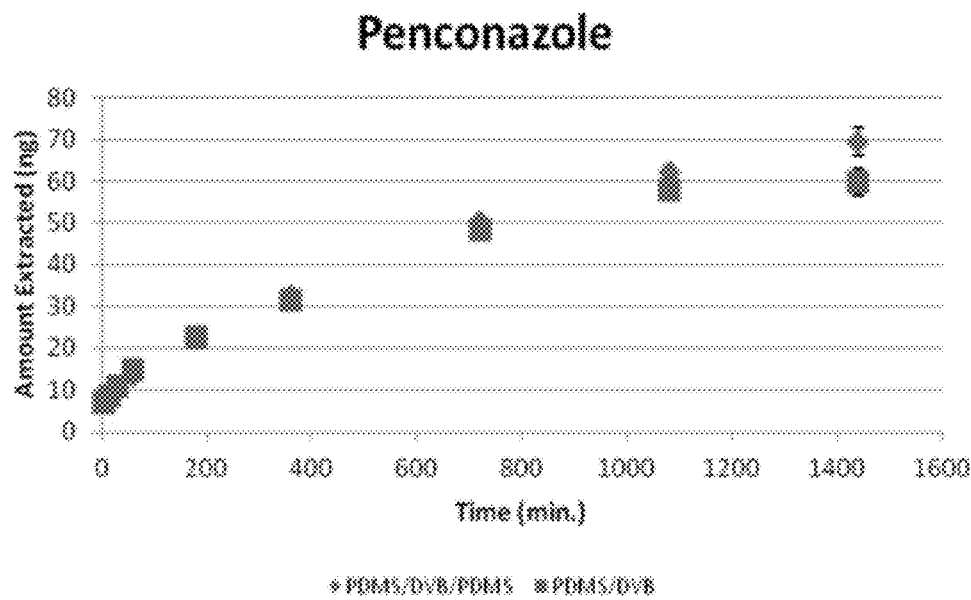
Figure 5C:
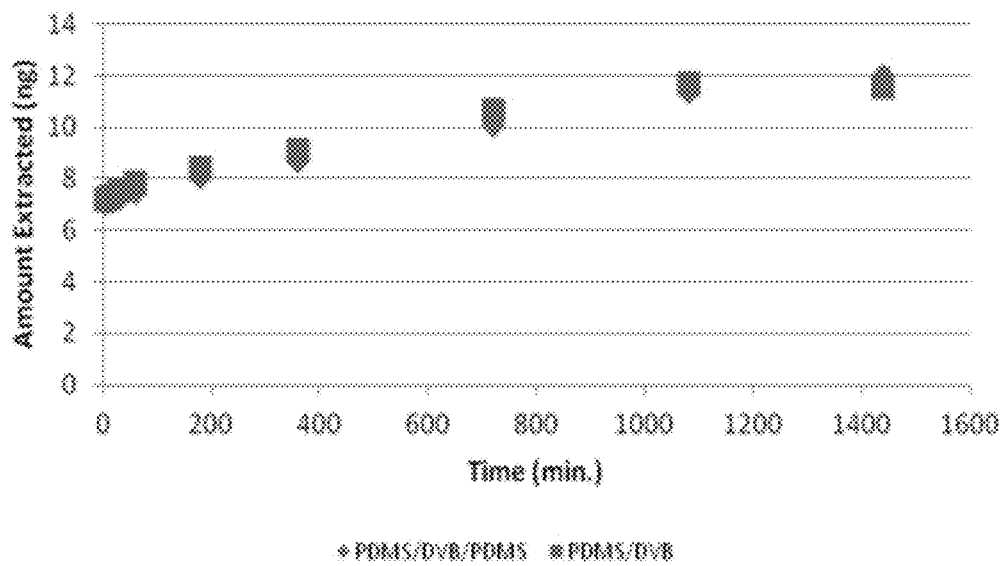
Figure 5D:
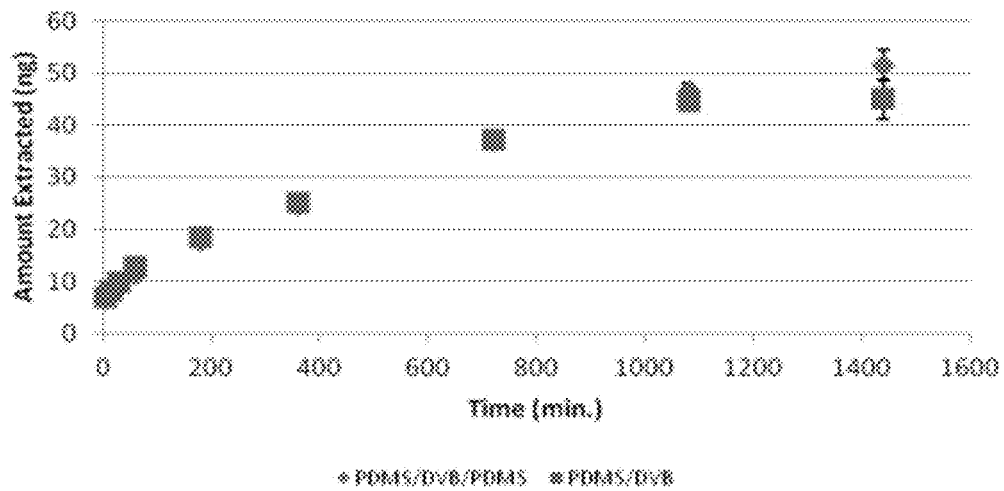
Figure 5E:
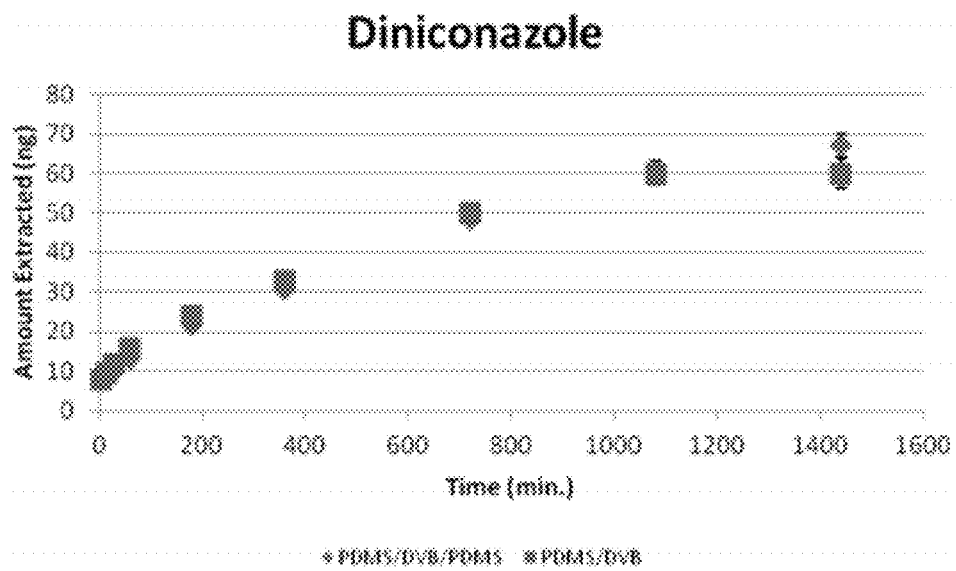

Additionally, as it can be seen in FIG. 4, which illustrates the comparative extraction equilibration for BTEX compounds obtained with the commercial PDMS/DVB and the PDMS coated PDMS/DVB fibre (PDMS/DVB/PDMS), the amount of analyte extracted at equilibrium or near equilibrium by the PDMS coated PDMS/DVB fibre is higher than the amount extracted by the commercial PDMS/DVB fibre. This effect is more pronounced as the partitioning coefficient in PDMS increases, but the equilibration times also become longer as well. It can be seen that for benzene the amount extracted by both fibres did not statistically differ, whereas, for o-xylene the PDMS-coated SPME fibre has extracted around 20% more as compared to commercial PDMS/DVB fibre. In fact, PDMS-coated SPME fibre presents a higher total volume when compared to the original fibre. The additional PDMS layers has a volume of about 0.260 µL (assuming average PDMS layer thickness of 27.5 µm) rendering the coating a total volume of about 0.700 µL against the 0.440 µL presented by the commercial PDMS/DVB stableflex fibre.

In the PDMS coated PDMS/DVB fibre, the PDMS layer does not only play a role as a barrier slowing down the kinetics of extractions but also acts as an additional extraction phase for analyte concentration, hence, changing the total analyte capacity of the coating. In the PDMS coated PDMS/DVB fibre, the total equilibrium amount of the analyte extracted is the sum of its amounts in both layers. In contrast to the standard membrane techniques, analytes in the PDMS outer layer phase is also transferred to the gas chromatograph injection port since PDMS is part of the probe. Moreover, the result obtained suggests that there was no blockage of the extraction sites on the surface of the original PDMS/DVB coating by the additional PDMS layer, thus, with no impairing of extraction capabilities of the original coating.

EXAMPLE 5

Evaluation of PDMS Coating on an SPME Fibre

The extraction profiles of triazoles pesticides in the commercial PDMS/DVB fibre and in the PDMS coated PDMS/DVB fibre were used to determine if the additional layer of PDMS affected the extraction of the triazoles pesticides. If different extraction profiles were found for the two fibres, then the additional layer of PDMS would be determined to affect the extraction of triazoles pesticides in the overall extraction process. In contrast, if the extraction profiles were found to be similar for the two fibres, then the additional layer of PDMS would be determined to not affect the extraction of triazoles pesticides in the overall extraction process.

An aliquot of 18 mL of an aqueous solution containing approximately 5.5 μg/L of each triazole was placed in a 20-mL vial. A 5 min incubation of the sample was performed on the stir plate while stirring at 1200 rpm and at 30° C. Extraction time ranged from 5 min to 1440 min. Following extraction, the fibre was placed in the GC injection port for desorption for 7 min at 260° C. All extraction time points were performed in duplicate. The results are illustrated in FIG. 5. Although the additional layer of PDMS affects the extraction of BTEX compounds, as discussed in Example 4, it was surprisingly determined that the additional layer of PDMS did not affect the extraction of triazoles pesticides in the overall extraction process.

FIG. 5 shows extraction time profiles for triazoles pesticides obtained with commercial and PDMS coated PDMS/DVB fibre. The comparison of both extraction time profiles for penconazole presented in FIG. 5B illustrates that, in corroboration with the findings for BTEX extractions, only marginal differences could be observed at shorter extraction times as a result of the additional step of diffusion of the analytes through the thin PDMS outer layer.

Although, Kloskoeski et al. (Membrane solid-phase microextraction—A new concept in sorbent preparation. *Analytical Chemistry.* 2009, Vol. 81, pp. 7363-7367) presented a system comprised of polyethylene glycol (PEG) coating restricted within a PDMS outer layer. The authors referred to the system as a membrane-SPME, and reported that the external layer of PDMS of 25 μm significantly slowed down the diffusion of the polar analytes across the PDMS membrane, which could serve as a physical barrier as well as a concentrating medium, analogous to the extraction phase.

However, the results illustrated in FIG. 5 indicate that the PDMS layer is not substantially changing the kinetic and thermodynamic parameters associated to the original PDMS/DVB fiber coating. Hence, it is to be understood that mass transfer through the boundary layer surrounding the outer PDMS layer controls the overall mass transfer in the present studied system for analytes of these characteristics.

EXAMPLE 6

Robustness and Reusability

One of the problems which may be encountered with existing commercial SPME coatings applied in food analysis is the fouling of the commercial coatings on exposure to highly complex matrices. Accordingly, the stability of the PDMS coated PDMS/DVB fibre over the time was also determined.

To determine endurance and reusability, the PDMS coated PDMS/DVB fibre was subjected to a series of 130 successive direct immersion SPME cycles in whole grape pulp. Each cycle consisted of 15 min extraction at 30° C.; 50 s rinsing in de-ionized water prior to desorption; 7 min desorption at 260° C.; post-desorption washing in de-ionized water for 2.5 min; and 2.5 min fibre conditioning at 250° C. at autosampler conditioning station device.

The PDMS coated PDMS/DVB fibre was inspected under electronic microscope every 10 cycles and, when needed, manually freed of any possible debris attached to its surface by wiping using a KimWipe® tissue.

Figure 6:
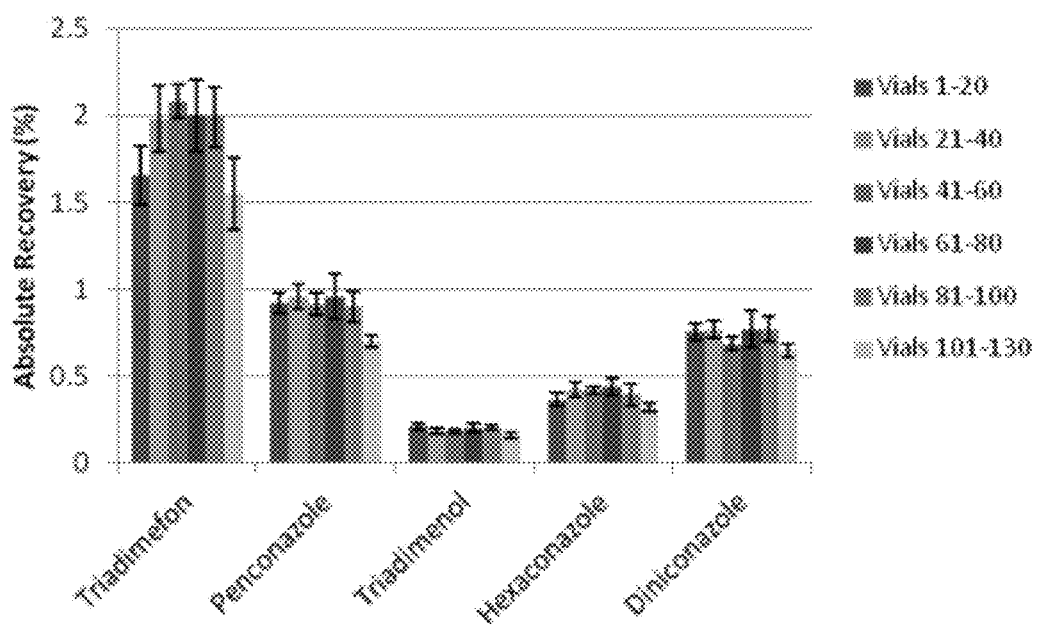
FIG. 6 is a graph which illustrates extraction of triazole compounds over successive DI-SPME cycles by a PDMS coated SPME fibre according to one aspect of the disclosure.

No irreversible damage on the surface was observed. Moreover, QCs consisting of water samples spiked with triazole pesticides were distributed along the batch to ensure that the fibre performance was not altered. The results are illustrated in FIG. 6 and shows that the fibre endurance measured as the amount of analyte extracted throughout the experiment has a relative standard deviation below 20%. Taking into account the complexity of the studied matrix, this value is an impressive achievement with performance much superior to that exhibited by the original commercial fibre. For instance, De Jager et al. (L. S De Jager, G. A. Perfetti, G. W. Diachenko. Analysis of tetramethylene disulfotetramine in foods using solid-phase microextraction-gas chromatography-mass spectrometry. *Journal of Chromatography A.* 2008, Vol. 1192, pp. 36-40) reported a 65% drop in signal by the 10th extraction when analyzing food samples diluted in water using PDMS/DVB fibre in DI-SPME mode.

In the preceding description, for purposes of explanation, numerous details are set forth in order to provide a thorough understanding of the examples. However, it will be apparent to one skilled in the art that these specific details are not required. The above-described examples are intended to be exemplary only. Alterations, modifications and variations can be effected to the particular examples by those of skill in the art without departing from the scope, which is defined solely by the claims appended hereto.

REFERENCES

1. R. M. Gonzalez-Rodriguez, B. Cancho-Grande, J. Simal-Gandara. Multiresidue determination of 11 new fungicides in grapes and wines by liquid-liquid extraction/clean-up and programmable temperature vaporization injection with analyte protectants/gas chromatography/ion trap mass spectrometry. Journal of Chromatography A. 2009, Vol. 1216, pp. 6033-6042.
2. K. Baneriee, D. P. Oulka, S. Dasgupta, S. B. Patil, S. H. Patil, R. Savant, P. G. Adsule. Validation and uncertainty analysis of a multi-residue method for pesticides in grapes using ethyl acetate extraction and liquid chromatography-tandem mass spectrometry. Journal of Chromatography A. 007, Vol. 1173, 1-2, pp. 98-109.
3. V. Guillet, C. Fave, M. Montury. Microwave/SPME method to quantify pesticides residues in tomato fruits. Journal of Environmental Science and Health Part B. 2009, Vol. 44, pp. 415-422.
4. J. Oliva, A. Barba, N. Vela, F. Melendreras, S. Navarro. Multiresidue method for the rapid determination of organophosphorous insecticides in grapes, must and wine. Journal of Chromatography A. 2000, Vol. 882, pp. 213-220.
5. J. Oliva, S. Navarro, A. Barba, G. Navarro. Determination of chlorpyrifos, penconazole, fenarimol, vinclozolin and metalaxyl in grapes, must and wine by on-line microextraction and gas chromatogaphy. Journal of Chromatography A. 1999, Vol. 833, pp. 43-51.
6. A. J. A. Charlton, A. Jones. Determination of imisazole and triazole fungicide residues in honeybees using gas chromatography-mass spectrometry. Journal of Chromatography A. 2007, 1141, pp. 117-122.
7. J. Zeng, J. i Chen, Z. Lin, W. Chen, X. Chen, X. Wang. Development of polydimethylphenylsiloxane-coated fiber for solid-phase microextraction and its analytical application of qualitative and semi-quantitative of organochlorine and pyrethroid pesticides in vegetables. Analytica Chimica Acta. 2008, Vol. 619, pp. 59-66.
8. M. Anastassiades, S. J. Lehotay, D. Stajnbaher, F. J. Schenck. Fast and easy multiresidue method employing acetonitrile extraction/partitioning and "dispersive solid-phase extraction" for the determination of pesticide residues in produce. Journal of AOAC International. 2003, Vol. 86, 2, pp. 412-431.
9. D. Steiniger, G. P. Lu, J. Butler, E. Phillips, Y. Fintschenko. Determination of Multiresidue Pesticides in Green Tea by Using a Modified QuEChERS Extraction and Ion-Trap Gas Chromatography/Mass Spectrometry. Journal of AOAC International. 2010, Vol. 93, 4, pp. 1169-1179.
10. S. C. Cunha, J. O. Fernandes, A. Alves, M. B. P. P. Oliveira. Fast low-pressure gas chromatography-mass spectrometry method for the determination of multiple pesticides in grapes, must and wines. Journal of Chromatography A. 2009, Vol. 1216, pp. 119-126.
11. Wong J, C. Y. Hao, K. Zhang, P. Yang, K. Banerjee, D. Hayward, I. Iftakhar, A. Schreiber, K. Tech, C. Sack C, M. Smoker, X. R. Chen, S. C. Utture, D. P. Oulka. Development and Interlaboratory Validation of a QuEChERS-Based Liquid Chromatography-Tandem Mass Spectrometry Method for Multiresidue Pesticide Analysis. Journal of Agricultural and Food Chemistry. 2010, Vol. 58, 10, pp. 5897-5903.
12. P. Paya, M. Anastassiades, D. Mack, I. Sigalova, B. Tasdelen, J. Oliva, A. Barba. Analysis of pesticide residues using the Quick Easy Cheap Effective Rugged and Safe (QuEChERS) pesticide multiresidue method in combination with gas and liquid chromatography and tandem mass spectrometric detection. Analytical and Bioanalytical Chemistry. 2007, Vol. 389, 6.
13. Pawliszyn, J. SPME Method Development. Solid Phase Microextraction: Theory and Practice. 1. New York: Wiley-VCH, 1997, pp. 97-139.
14. S. Risticevic, H. Lord, T. Gorecki, C. L. Arthur, J. Pawliszyn. Protocol for solid phase microextraction method development. Nature Protocols. 2010, Vol. 5, 1, pp. 122-139.
15. J. Schurek, T. Portoles, J. Hajslova, K. Riddellova, F. Hernandez. Application of head-space solid-phase microextraction coupled to comprehensive two-dimensional gas chromatography-time-of-flight mass spectrometry for the determination of multiple pesticide residues in tea samples. Analytica Chimica Acta. 2008, Vol. 611, 2, pp. 163-172.
16. D. A. Lambropoulou, T. A. Albanis. Headspace solid-phase microextraction in combination with gas chromatography-mass spectrometry for the rapid screening of organophosphorus insecticide residues in strawberries and cherries. Journal of Chromatography A. 2003, Vol. 993, 1-2, pp. 197-203.
17. M. Natangelo, S. Tavazzi, E. Benfenati. Evaluation of solid phase microextraction-gas chromatography in the analysis of some pesticides with different mass spectrometric techniques: Application to environmental waters and food samples. Analytical Letters. 2002, Vol. 35, 2, pp. 327-338.
18. W. Chen, KF Poon, M. H. W. Lam. The application fo solid phase microextraction in the analysis of organophosphorous pesticides in a food plant. Environmental Science & Technology. 1998, Vol. 32, 23, pp. 3816-3820.
19. K. Fytianos, N. Raikos, G. Theodoridis, Z. Velinova, H. Tsoukali. Solid phase microextraction applied to the analysis of organophosphorous insecticides in fruits. Chemosphere. 2006, Vol. 65, pp. 2090-2095.
20. A. Menezes Filho, F, N. Santos, P. A. P. Pereira. Development, validation and application of a maethodology based on solid-phase micro extraction followed by gas chromatography coupled to mass spectrometry (SPME/GC-MS) for the determination of pesticides residues in mangoes. Talanta. 2010, Vol. 81, pp. 346-354.
21. M. Volante, M. Pontello, L. Valoti, M. Cattaneo, M. Bianchi, L. Colzani. Application of solid phase microextraction (SPME) to the analysis of pesticides residues in vegetables. Pest Management Science. 2000, Vol. 56, pp. 618-636.
22. H. L. V. Capobiango, Z. L. Cardeal. A solid phase microextraction method for the chromatographic determination of organophosphorous pesticides in fish, water, potatoes, guava and coffee. Journal of Brazilian Chemical Society. 2005, Vol. 16, 5, pp. 907-914.
23. C. G. Zambonin, M. Quinto, N. De Vietro, F. Palmisano. Solid phase microextraction-gas chromatography mass spectrometry: A fast and simple screening method for the assessment of organophosphorous pesticides residues in wine and fruit juices. Food Chemistry. 2004, Vol. 86, pp. 269-274.
24. C. G. Zambonin, A. Cilenti, F. Palmisano. Solid phase microextraction and gas chromatography-mass spectrometry for the rapid screening of triazole residues in wine and strawberries. Journal of Chromatography A. 2002, Vol. 967, pp. 255-260.
25. A. Aguinaga, N, Campillo, P. Vinas, M. Hernadez-Cordoba. Solid phase mciroextraction coupled to gas chromatography-mass spectrometry for the analysis of famoxadone in wines, fruits and vegetables. Spectroscopy Letters. 2009, Vol. 42, pp. 320-326.
26. R. Hu, B. Hennion, L. Urruty, M. Montury. Solid phase microextraction of pesticide residues from strawberries. Food Additives and Contaminants. 1999, Vol. 16, 3, pp. 111-117.
27. P. Vinas, N. Campillo, N. Martinez-Castillo, M. Hernandez-Cordoba. Method development and validation for strobilurin fungicides in baby foods by solid phase microextraction gas chromatography-mass spectrometry. Journal of Chromatography A. 2009, Vol. 1216, pp. 140-146.
28. K. Ridgway, S. P. D. Lalljie, R. M. Smith. Sample preparation techniques for the determination of trace residues and contaminants in food. Journal of Chromatography A. 2007, Vol. 1153, pp. 36-53.
29. F. Augusto, E. Carasek. R. G. C. Silva, S. R. Rivellino, A. D. Batista, E. Martendal. New sorbents for extraction and microextraction techniques. Journal of Chromatography A. 2010, Vol. 1217, pp. 2533-2542.
30. L. Cai, S. Gong, M. Chen, C. Wu. Vinyl crown ether as a novel radical crosslinked sol-gel SPME fiber for determination of organousphosphorous pesticides in food samples. Analytica Chimica Acta. 2006, Vol. 559, pp. 89-96.
31. D. Djozan, M. Mahkam, B. Ebrahimi. Preparation and biding study of solid phase microextraction fiber on the basis of ametryn-imprinted polymer—Application to the selective extraction of persistent triazine herbicides in tap water, rice, maize and onion. Journal of Chromatography A. 2009, Vol. 1216, pp. 2211-2219.
32. E. Turiel, J. L. Tadeo, A. Martin-Esteban. Molecularly imprinted polymeric fibers for solid phase microextraction. Analytical Chemistry. 2007, Vol. 79, pp. 3099-3104.
33. C. Dietz, J. Sanz, C. Camara. Recent developments in solid phase microextarction coatings and related techniques. Journal of Chromatography A. 2006, Vol. 1103, pp. 183-192.
34. J. Beltran, F. J. Lopez, F. Hernandez. Solid-phase microextraction in pesticide residue analysis. Journal of Chromatography A. 2000, Vol. 885, pp. 389-404.
35. A. Jahnke, P. Mayer. Do complex matrices modify the sorptive properties of polydimethylsiloxane (PDMS) for non-polar organic chemicals. Journal of Chromatography A. 2010, Vol. 1217, 29, pp. 4765-4770.
36. D. Vuckovic, R. Shirey, Y. Chen, L. Sidisky, C. Aurand, K. Stenerson, J. Pawliszyn. In vitro evaluation of new biocompatible coatings for solid-phase microextraction: Implications for drug analysis and in vivo sampling applications. Analytica Chimica Acta. 2009, Vol. 638, pp. 175-185.
37. L. S De Jager, G. A. Perfetti, G. W. Diachenko. Analysis of tetramethylene disulfotetramine in foods using solid-phase microextraction-gas chromatography-mass spectrometry. Journal of Chromatography A. 2008, Vol. 1192, pp. 36-40.
38. A. L. Simplicio, L. V. Boas. Validation of a solid-phase microextraction method for the determination of organophosphorous pesticides in fruits and fruit juice. Journal of Chromatography A. 1999, Vol. 833, pp. 35-42.
39. A. Kloskowski, M. Pilarczyk. Membrane solid-phase microextraction—A new concept in sorbent preparation. Analytical Chemistry. 2009, Vol. 81, pp. 7363-7367.

What is claimed is:

1. A coated solid phase microextraction (SPME) fibre for use in direct immersion SPME of a food matrix that includes carbohydrates, the coated SPME fibre comprising:
    a SPME fibre having an extractive portion for absorbing a small molecule from the food matrix; and
    a protective coating that comprises polydimethylsiloxane (PDMS) or polyfluorocarbons and that is between about 10 µm and about 40 µm thick, wherein the protective coating covers the extractive portion of the SPME fiber and wherein the protective coating has an exposed surface that is substantially uniform and substantially smooth, the protective coating reducing adsorption of the carbohydrates onto the SPME fibre and allowing the SPME fibre to extract the small molecule from the food matrix,
    wherein the substantially uniform, substantially smooth surface of the protective coating has, on average fewer than 2 imperfections greater than 10 nm in length per 1000 nm$^2$ of protective coating, as seen on a 900× magnification of an Electron Scanning Microscope.

2. The coated SPME fibre according to claim 1, wherein the surface of the protective coating is substantially non-porous.

3. The coated SPME fibre according to claim 1, wherein: the SPME fibre is a commercially available SPME fibre; or the SPME fibre comprises a bonding polymer adhering together SPME particles which have pores for absorbing the small molecule from the food matrix.

4. The coated SPME fibre according to claim 1, wherein
    the substantially uniform, substantially smooth surface of the protective coating has, on average:
    fewer than 1 imperfections greater than 10 nm in length per 1000 nm$^2$ of protective coating, as seen on a 900× magnification of an Electron Scanning Microscope, or
    fewer than 0.1 imperfections greater than 10 nm in length per 1000 nm$^2$ of protective coating, as seen on a 900× magnification of an Electron Scanning Microscope;
    or wherein the substantially uniform, substantially smooth surface of the protective coating has no observable imperfections when viewed at 900× magnification using an Electron Scanning Microscope.

5. The coated SPME fibre according to claim 1, wherein the food matrix is selected from the group consisting of fruit pulp, fruit juice, vegetable pulp, vegetable juice, and any combination thereof.

6. The coated SPME fibre according to claim 1, wherein the small molecule is a hydrophobic or hydrophilic molecule having a molecular mass less than about 10,000 atomic mass units.

7. The coated SPME fibre according to claim 1, wherein the small molecule is a triazole pesticide.

8. A method of direct immersion solid phase microextraction (DI-SPME) of a small molecule from a food matrix that includes carbohydrates, the method comprising:
    providing the food matrix;
    immersing a coated solid phase microextraction (SPME) fibre according to claim 1 into the food matrix;
    removing the coated SPME fibre from the food matrix; and
    analyzing the small molecule extracted from the food matrix by chromatography.

9. The method according to claim 8 where the chromatography is gas chromatography.

10. The method according to claim 8, wherein the small molecule is a triazole pesticide.

11. The method according to claim 8, wherein the food matrix is selected from the group consisting of fruit pulp, fruit juice, vegetable pulp, vegetable juice, and any combination thereof.

12. The method according to claim 8, wherein
    the substantially uniform, substantially smooth surface of the protective coating has, on average:
    fewer than 1 imperfections greater than 10 nm in length per 1000 nm$^2$ of protective coating, as seen on a 900× magnification of an Electron Scanning Microscope, or
    fewer than 0.1 imperfections greater than 10 nm in length per 1000 nm$^2$ of protective coating, as seen on a 900× magnification of an Electron Scanning Microscope;
    or wherein substantially uniform, substantially smooth surface of the protective coating has no observable imperfections when viewed at 900× magnification using an Electron Scanning Microscope.

13. The coated SPME fibre according to claim 1, wherein the SPME fiber comprises divinylbenzene as an extractive material.

14. The coated SPME fibre according to claim 1, wherein the protective coating comprises polydimethylsiloxane (PDMS).

15. The coated SPME fibre according to claim 1, wherein the small molecule is selected from the group consisting of: triadimefon, penconazole, triadimenol, hexaconazole, and diniconazole.

* * * * *